(12) United States Patent
Asehnoune et al.

(10) Patent No.: US 12,377,126 B2
(45) Date of Patent: Aug. 5, 2025

(54) ALGAL EXTRACT FOR USE IN THE TREATMENT OR PREVENTION OF POST-TRAUMATIC IMMUNOSUPPRESSION

(71) Applicant: AMADEITE, Brehan (FR)

(72) Inventors: Karim Asehnoune, Nantes (FR); Cédric Jacqueline, Vallons-de-l'Erdre (FR); Marwan Bouras, Nantes (FR); Antoine Roquilly, Nantes (FR); Pi Nyvall-Collén, Roscoff (FR); Hervé Demais, Merlevenez (FR); Hervé Balusson, Brehan (FR)

(73) Assignee: AMADEITE, Brehan (FR)

( * ) Notice: Subject to any disclaimer, the term of this patent is extended or adjusted under 35 U.S.C. 154(b) by 1113 days.

(21) Appl. No.: 17/286,999

(22) PCT Filed: Oct. 22, 2019

(86) PCT No.: PCT/EP2019/078757
§ 371 (c)(1),
(2) Date: Apr. 20, 2021

(87) PCT Pub. No.: WO2020/083931
PCT Pub. Date: Apr. 30, 2020

(65) Prior Publication Data
US 2021/0386808 A1 Dec. 16, 2021

(30) Foreign Application Priority Data
Oct. 22, 2018 (FR) ...................................... 18 59721

(51) Int. Cl.
*A61K 36/05* (2006.01)
*A61P 37/02* (2006.01)

(52) U.S. Cl.
CPC .............. *A61K 36/05* (2013.01); *A61P 37/02* (2018.01); *A61K 2236/13* (2013.01); *A61K 2236/15* (2013.01); *A61K 2236/51* (2013.01); *A61K 2236/53* (2013.01)

(58) Field of Classification Search
CPC .................................................... A61K 36/06
See application file for complete search history.

(56) References Cited

U.S. PATENT DOCUMENTS

| | | | | |
|---|---|---|---|---|
| 10,821,144 B2 * | 11/2020 | Demais | .................... | A61P 25/04 |
| 10,912,805 B2 * | 2/2021 | Demais | .................... | A61P 37/02 |
| 11,633,443 B2 * | 4/2023 | Demais | .................. | A61K 36/05 |
| | | | | 424/195.17 |
| 2013/0028936 A1 | 1/2013 | Asehnoune | | |
| 2013/0102662 A1 | 4/2013 | Darwiche et al. | | |
| 2016/0287648 A1 | 10/2016 | Demais | | |

FOREIGN PATENT DOCUMENTS

| | | | |
|---|---|---|---|
| CN | 105873596 A | 8/2016 | |
| FR | 2 954 703 | 7/2011 | |
| FR | 2 999 084 | 6/2014 | |
| FR | 3013223 A1 * | 5/2015 | ............. A61K 36/05 |
| JP | 2005526500 A | 9/2005 | |
| JP | 2007525426 A | 9/2007 | |
| JP | 2008546808 A | 12/2008 | |
| JP | 2010538282 A | 12/2010 | |
| JP | 2016539184 A | 12/2016 | |
| KR | 20100031252 A | 3/2010 | |
| WO | 03071877 A1 | 9/2003 | |
| WO | 2004093897 A1 | 11/2004 | |
| WO | 2007002570 A1 | 1/2007 | |
| WO | 2009030456 A1 | 3/2009 | |
| WO | 2010/115149 | 10/2010 | |
| WO | 2011/080126 | 7/2011 | |
| WO | 2015/071497 | 5/2015 | |
| WO | 2015/071502 | 5/2015 | |

OTHER PUBLICATIONS

Nainu, F. et al. "In vivo Antibacterial activity of green algae *Ulva reticulata* against *Staphylococcus aureus* in *Drosophila* model of infection", Pharmacogn J. Sep.-Oct. 2018; 10(5): 993-997. (Year: 2018).*
Villavicencio, R. et al. "The Pathogenesis of *Staphylococcus aureus* in the the trauma patient and potential future therapies", Am J of Surgery, 1996, vol. 172, p. 291-296. (Year: 1996).*
Roquilly et al., "Post-Traumatic Immunodepression: From Pathology to Treatment", Reanimation, Jan. 28, 2015, vol. 24, No. 2, pp. S285-S290 (6 total pages).
International Search Report for PCT/EP2019/078757 dated Feb. 10, 2020, 7 pages.
Written Opinion of the ISA for PCT/EP2019/078757 dated Feb. 10, 2020, 7 pages.
Araujo et al. "Analgesic and anti-inflammatory actions on bradykinin route of a polysulfated fraction from alga Ulva Lactuca", International Journal of Biological Macromolecules, 2016, vol. 92, pp. 820-830.
Berri et al., "Marine-sulfated polysaccharides extract of Ulva armoricana green algae exhibits an antimicrobial activity and stimulates cytokineexpression by intestinal epithelial cells", Journal of Applied Phycology, 2016, vol. 28, pp. 2999-3008.
Berri et al., "Ulvan from *Ulva armoricana* (Chlorophyta) activates the PI3K/Akt signalling pathway via TLR4 to induce intestinal cytokine production", Algal Research, 2017, vol. 28, pp. 39-47.
Coller et al., "A New Option for Immune Stimulation: Seaweed Polysaccharides", Feed Research, 2014, No. 5, pp. 30-33.
Heffernan et al., "Failure to normalize lymphopenia followingtrauma is associated with increased mortality, independent of the leukocytosis pattern", Critical Care, 2012, vol. 16, pp. 1-10.
Quan et al., "Roles of Toll-Like Receptors in Post-Traumatic Inflammatory Response", Progress in Physiological Sciences, 2010, vol. 4, No. 3, pp. 221-223.

(Continued)

*Primary Examiner* — Gina C Justice
(74) *Attorney, Agent, or Firm* — NIXON & VANDERHYE

(57) ABSTRACT

Disclosed is an extract of algae of the order Ulvales, including sulfated and non-sulfated polyanionic polysaccharides, the molecular weight of which is less than or equal to 50 kDa, for use in the prevention and/or treatment of complications caused by post-traumatic immunosuppression.

20 Claims, 13 Drawing Sheets

(56) References Cited

OTHER PUBLICATIONS

Figure 1:
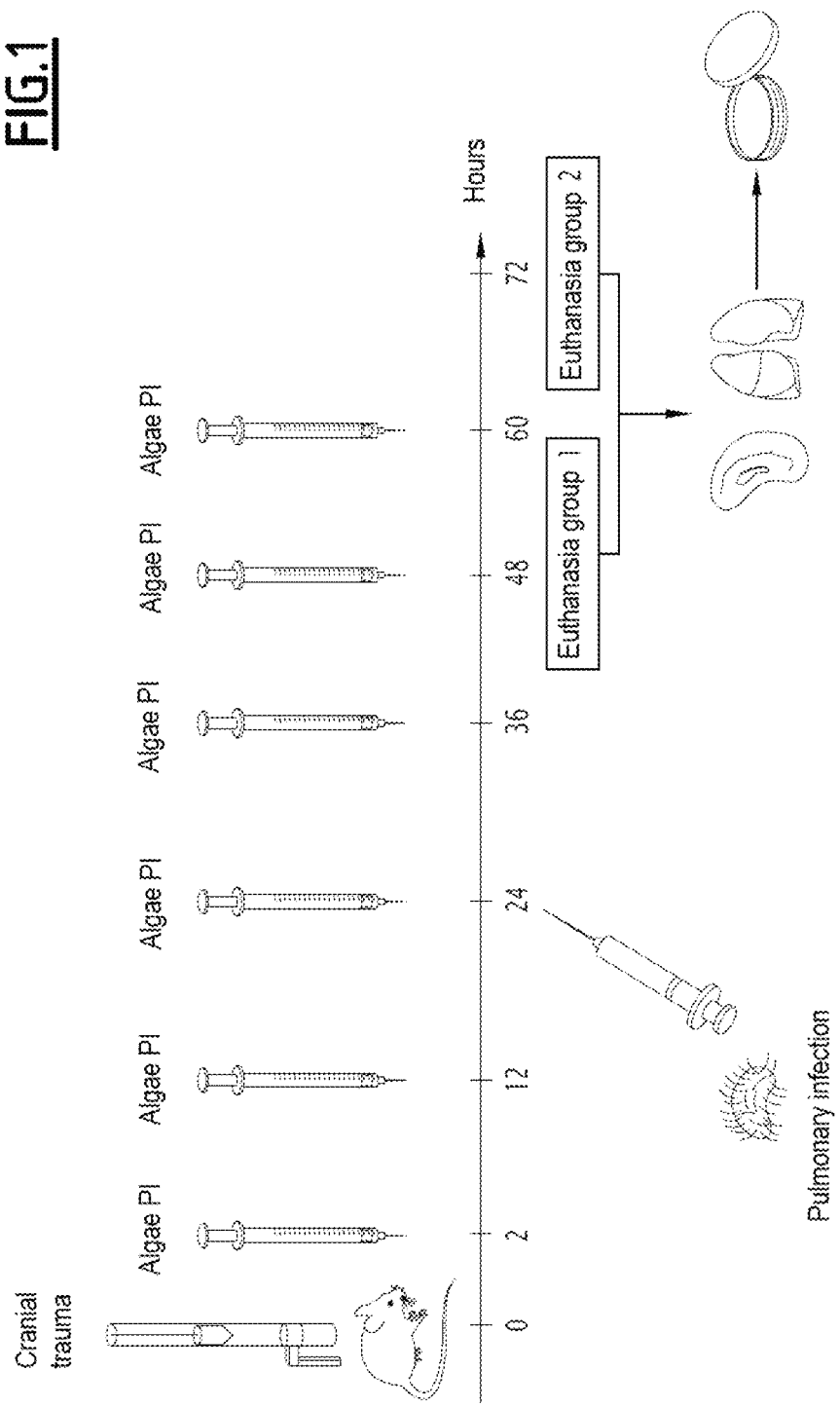

Roquilly et al., "CpG-ODN and MPLA Prevent Mortality in a Murine Modelof Post-Hemorrhage—*Staphyloccocus aureus* Pneumonia", PLoS One, Oct. 2010, vol. 5, Issue 10, e13228, pp. 1-12.
Roquilly et al., "Toll-like receptor-4 agonist in post-haemorrhage pneumonia: role of dendritic and natural killer cells", European Respiratory Journal, 2013, vol. 42, pp. 1365-1378.
Zhou et al., "Immunomodulatory activity of a novel polysaccha ride from Lonicerajaponica in immunosuppressed mice induced by cyclophosphamide", PLoS One, Oct. 2018, vol. 13, e0204152, pp. 1-15.

* cited by examiner

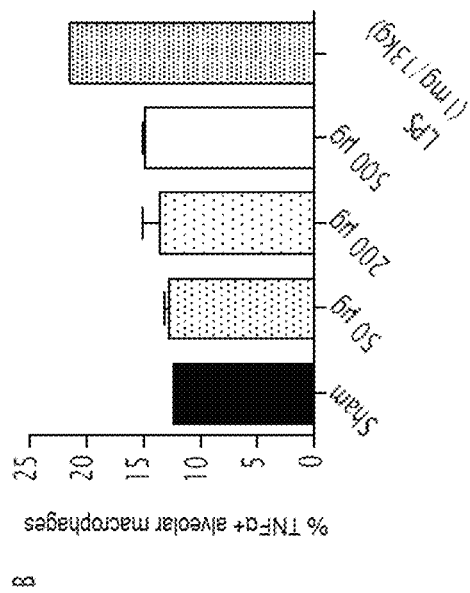
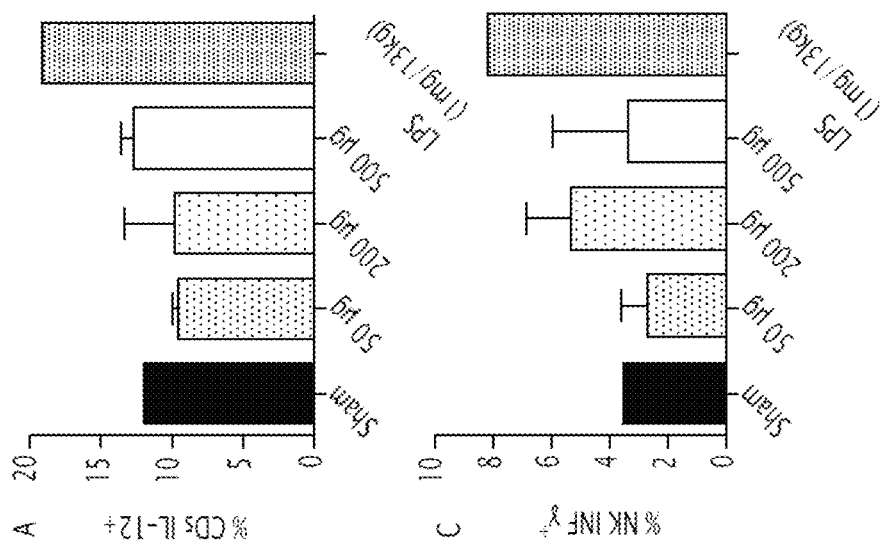
FIG. 5

ALGAL EXTRACT FOR USE IN THE TREATMENT OR PREVENTION OF POST-TRAUMATIC IMMUNOSUPPRESSION

CROSS-REFERENCE TO RELATED APPLICATIONS

This application is the U.S. national phase of International Application No. PCT/EP2019/078757 filed Oct. 22, 2019 which designated the U.S. and claims priority to FR 18 59721 filed Oct. 22, 2018, the entire contents of each of which are hereby incorporated by reference.

BACKGROUND OF THE INVENTION

Field of the Invention

The present invention relates to an extract of algae of the order Ulvales comprising sulfated and non-sulfated polyanionic polysaccharides, the molecular weight of which is less than or equal to 50 kDa, for use in the prevention and/or treatment of complications induced by post-traumatic immunosuppression.

Description of the Related Art

Polytrauma (multiple trauma) or severe trauma is accompanied by a systemic inflammatory response syndrome (SIRS) caused by the release of intracellular components referred to as "danger-associated molecular patterns" (DAMPs). These DAMPs will directly stimulate specific receptors, the "pattern recognition receptors", present on the cells of the immune system, thereby causing the release of mediators of inflammation (inflammatory mediators). In order to avoid systemic complications from uncontrolled SIRS, the body develops an early systemic compensatory anti-inflammatory response syndrome (CARS). CARS leads to post-traumatic immunosuppression that varies in duration and magnitude. At the outset this immunosuppression is "physiological" and present in all patients. The immunosuppression becomes pathological if it persists, leading to post-traumatic infections (mainly pneumopathies) which are the primary cause of complications in intensive care (Roquilly et al., 2015, Reanimation [Intensive Care Medicine], 24: S285-S290).

Cranial trauma (or head trauma) is a major cause of morbidity and mortality, with an overall mortality rate for victims varying between 5 and 25 per 100,000 patients. About one third of the morbidity and mortality factors are avoidable complications that occur in intensive care (infections, thromboembolic events), mainly due to respiratory complications. The morbidity and health costs caused by pneumonia acquired under mechanical ventilation, ie ventilator-associated pneumonia (VAPs) make it one of the complications most related to the care provided. Between 40 and 60% of patients with severe cranial trauma hospitalised in intensive care units will have VAP, with about 50% thereof being caused by methicillin-suscitible *Staphylococcus aureus* (MSSA). During their hospitalisation in intensive care, a cranial trauma patient suffering from VAP will have more cerebral injuries of systemic origin (fever, hypotension, hypoxia, hypercapnia); the duration of mechanical ventilation will also be extended, as well as the stay in intensive care. All these factors contribute on the one hand to the appearance of new hypoxic ischemic brain injuries, and on the other hand to a delay in post-intensive care management (rehabilitation and the like). The development of a VAP in a cranial trauma patient is therefore an independent factor of risk of undesirable long term neurological outcomes. The susceptibility of cranial trauma patients to nosocomial infections and in particular to VAP is due to the appearance of post-traumatic immunosuppression.

At the cellular level, this post-traumatic immunosuppression is brought about on several levels:

1. Impairment of antigen presentation capability by antigen presenting cells (APCs), mainly Dendritic Cells (DCs) and monocytes. DCs play a central role in capturing and presenting the antigen, as well as in activating the lymphocytes (T and NK) via the secretion of pro-inflammatory cytokines (Interleukin-12).
2. A decrease in the capacity to secrete pro-inflammatory cytokines. Cooperation between APCs and lymphocytes in case of acute lung injuries is essential. Thus, an alteration in the production of IL-12, a consequence of cranial trauma will induce a decrease in secretion of pro-inflammatory cytokines such as INF γ by lymphoid cells (Spolarics et al., 2003, Crit. Care Med.; 31(6): 1722-9). On the other hand, the increase in the secretion of anti-inflammatory cytokines (IL-10) via sympathetic hyper-activation contributes to deepening this state of immunosuppression (Roquilly et al., 2014, Crit. Care Med., 42 (12): 752-61). The alteration of this "loop" of the innate immune response therefore causes a decrease in the body's ability to fight secondary infections.
3. Exhaustion of T lymphocytes ("T cell exhaustion"), a phenomenon also found in post-septic immunosuppression. This exhaustion corresponds to the progressive loss of pro-inflammatory functions of the lymphocytes in the presence of a high antigen load. This phenomenon would serve to explain in part the high incidence of VAP in cranial trauma patients. This "exhaustion" phenomenon and the resulting lymphopenia is a factor of risk of mortality in polytrauma (multiple trauma) patients (Heffernan et al., 2012, Crit. Care., 20; 16(1): R12). In most patients, this lymphopenia moreover persists beyond 6 months.

With the objective of correcting this post-traumatic immunosuppression, many therapies have been tested in recent years. They were aimed at either limiting the initial SIRS (and therefore the CARS) in particular through the use of low-dose glucocorticoids; or restoring the antigen presentation capacity or cytokine secretion capacity through the use of glucans, IFN y, GM-CSF or interleukin 12.

The "toll-like-receptors" (TLRs) are involved in the recognition of the danger-associated molecules (DAMPs). These receptors are located on the surface of cells of the innate immune system (innate immune cells). Ten different TLRs have been identified in humans, with each of them recognising one or more DAMPs. After recognition with its ligand, the TLR receptor can activate two major intracellular signalling pathways resulting in the activation i) of the transcription factor Nuclear Factor Kappa B (NF-κB, Myeloid differentiation factor 88 or MyD88-dependent pathway) leading to binding to the promoter of the genes of pro-inflammatory cytokines (Interleukin 12 [IL-12], tumor necrosis factor alpha [TNFα]); and ii) nuclear transcription factors of the family of IRFs (Interferon regulatory factor [IRF], TIR-domain-containing adapter-inducing interferon-β [TRIF] dependent pathway). The most studied receptors are TLR4, involved in the recognition of lipopolysaccharide (LPS) making up the wall of gram-negative bacilli, and TLR2, which recognises the lipoteichoic acid of gram-positive bacteria.

TLR agonists have been suggested as a possible avenue for research with the object being to restore immune functions that are "paralysed" by trauma and to fight secondary infections (Hedayat et al., 2011, Lancet Infect Dis.; 11(9): 702-12).

It has been shown that the administration of monophosphoryl lipid A (MPLA), a non-toxic derivative of LPS known to have TLR4 agonist activity, prevented mortality in a mouse model of post-haemorrhage pneumonia derived from hemorrhage-induced immunosuppressed mice (Roquilly et al. 2010, PLoS One 7; 5 (10): e13228; international patent application WO2011080126). However, the mechanism of action effectively involved therein has not been elucidated. In this mouse model of post-haemorrhage pneumonia derived from hemorrhage-induced immunosuppressed mice, it has also been shown that MPLA partially restores the function of dendritic cells (DCs); prevents overexpression of IL-10 mRNA in NK cells; and that the direct MPLA-stimulation of DCs decreases mortality, while the direct stimulation of NK cells would however appear to be dispensable in this immune response against pneumonia (Roquilly et al., 2013, Eur Respir J.; 42 (5): 1365-78). As admitted by the authors themselves, however, it has not been shown that this effect of MPLA is mediated by TLR4, in particular by TLR4 receptors expressed on the surface of DCs or NK cells.

Compounds based on marine algae are used in various fields ranging from the pharmaceutical industry to the microbiology field. Their biologically active components are mainly comprised of peptides, polyunsaturated fatty acids and polysaccharides. The cell walls of marine algae are rich in sulfated polysaccharides such as ulvans in green algae. Recently, it has been shown that a purified fraction of ulvans extracted from a green alga of the type *Ulva* has immunomodulatory activity, in particular in vitro on intestinal porcine epithelial cells IPEC-1 (patent application WO2015071497). In this IPEC-1 cell line, the algal extract stimulates the secretion of pro-inflammatory cytokines (IL1β, IL-6, IL-8, TNFα, and the like) in vitro (Berri et al., 2016, Journal of Applied Phycology, 28(5): 2999-3008), via the TLR4/NF-κB pathway (Berri et al., 2017, Algal Research, 28, 39-47).

The inventors have sought to determine whether an extract of algae of the order Ulvales, in particular green algae of the type *Ulva*, comprising sulfated and non-sulfated polyanionic polysaccharides the molecular weight of which is less than or equal to 50 kDa, could prevent or be effective in treating post-traumatic immunosuppression, in particular the respiratory complications thereof. The effects of this extract on pulmonary mucosal immunity were in particular evaluated in a mouse model of cranial (head) trauma (Flier) et al., 2009, Nat Protoc.; 4(9):1328-37), followed by pneumonia induced by methicillin-susceptible *Staphylococcus aureus* (MSSA).

It has thus been shown that, in the murine model of post-traumatic pulmonary bacterial infection, the algal extract:
- limits systemic (splenic) bacterial spread, without this effect being shown to be linked to a direct antibacterial action of the extract, thus indicating a restoration of the immune functions paralysed by the trauma;
- does not increase the proportion of innate immune cells that produce pro-inflammatory cytokines in the lung (IL-12 producing DCs, TNFα-producing macrophages, Interferon gamma (INFγ) producing NKs or T lymphocytes TLs);
- increases the number of total NK cells and the number of INFγ-producing NK cells, without increasing the percentage of INFγ$^+$ NK cells, in the lung (site of infection), but not in the spleen. This effect therefore offsets the decrease in the number of total NK cells and INFγ$^+$ NK cells in the lung, induced by the cranial trauma;
- has no effect on systemic bacterial spread when the mouse has undergone depletion of NK cells (>95% depletion of pulmonary NK cells);
- does not induce, in the lungs, any increase in the level of chemokines involved in the chemotaxis of NK cells When the pulmonary bacterial infection in the mice is induced in the absence of cranial trauma (and therefore without immunosuppression), the algal extract does not induce stimulation of innate immune cells, either via stimulation of IL-12 secretion by DCs, of TNFα by macrophages, or of INFγ by NKs or T lymphocyte cells (TLs); or via stimulation of membrane expression of major histocompatibility complex class II (MHC II) by DCs; and also does not limit bacterial spread.

Furthermore, the direct in vitro stimulation of pulmonary NK cells from naive or trauma subjected mice, with the alga extract does not induce any increase in the production of interferon γ or of the marker killer cell lectin-like receptor subfamily G member 1 (KLRG1) for activation of NK cells.

These results therefore demonstrate the utility value of an extract of algae of the order Ulvales, in particular green algae of the type *Ulva*, comprising sulfated and non-sulfated polyanionic polysaccharides the molecular weight of which is less than or equal to 50 kDa, for preventing or treating post-traumatic immunosuppression.

SUMMARY OF THE INVENTION

The invention relates to an extract of algae of the order Ulvales comprising sulfated and non-sulfated polyanionic polysaccharides the molecular weight of which is less than or equal to 50 kDa, for use in the prevention and/or treatment of complications induced by post-traumatic immunosuppression.

According to one embodiment, the complication induced is a septic complication associated with post-traumatic immunosuppression. According to certain embodiments, the septic complication is a nosocomial infection, in particular a nosocomial infection selected from the group consisting of pneumopathies, pneumonia acquired under mechanical ventilation, ie ventilator-associated pneumonia (VAPs), urinary tract infections, infections of central venous catheters, bacterial cerebromeningeal infections such as empyema, meningitis and brain abscess.

According to one embodiment, post-traumatic immunosuppression occurs as a consequence of one or more severe traumas, in particular a severe cranial trauma (head trauma).

The algal extract of the order ulvales is preferably an extract of green algae of the type *Ulva*.

According to one embodiment, the said sulfated and non-sulfated polyanionic polysaccharides the molecular weight of which is less than or equal to 50 kDa, have a molecular weight that is less than 15 kDa, and preferably greater than 500 Da. Preferably, the algal extract does not comprise sulfated or non-sulfated polyanionic polysaccharides having a molecular weight that is greater than 15 kDa.

According to one embodiment, the algal extract comprises:
mannose; and/or
arabinose; and/or
galactose; and/or glucose; and/or rhamnose; and/or xylose; and/or glucuronic acid.

According to one embodiment, the alga extract comprises:

from 10 to 50% carbon;

from 1 to 10% hydrogen;

from 1 to 5% nitrogen;

from 20 to 50% oxygen; and from 1 to 15% sulfur;

as a percentage by mass of the total dry matter (dry weight) of the algal extract.

According to one other embodiment, the algal extract is obtained by means of a method of preparation in which:

a) the algae are washed and desanded;

b) the said algae are ground;

c) the solid phase of the ground material is separated from its liquid phase;

d) the said liquid phase is clarified;

e) the juice obtained in step d) is ultra filtered through a membrane having pore size of 50 kDa or less; and f) the filtration juice obtained in step e) is concentrated and then dried.

DESCRIPTION OF THE PREFERRED EMBODIMENTS

According to one aspect, the invention relates to an extract of algae of the order Ulvales comprising sulfated and non-sulfated polyanionic polysaccharides, the molecular weight of which is less than or equal to 50 kDa, for use in the prevention and/or treatment of complications induced by post-traumatic immunosuppression.

According to one aspect, the invention relates to a treatment method for prophylactic or therapeutic treatment of complications induced by post-traumatic immunosuppression in a subject requiring the same, the method comprising of the administration to the said subject of an effective amount of an algal extract of the order Ulvales comprising sulfated and non-sulfated polyanionic polysaccharides the molecular weight of which is less than or equal to 50 kDa.

Extract of Algae of the Order Ulvales

An algal extract comprising sulfated and non-sulfated polyanionic polysaccharides with molecular weight less than or equal to 50 kDa has in particular been described in patent application WO2015071497.

The algal extract of the order Ulvales comprising sulfated and non-sulfated polyanionic polysaccharides the molecular weight of which is less than or equal to 50 kDa is in particular an extract of green algae of the type *Ulva*.

The term "green algae of the type *Ulva*" is understood to refer to the green algae grouped in the genus *Ulva*, of the family of Ulvaceae, of the order Ulvales. Mention may in particular be made of the following species and subspecies: *Ulva acanthophora, Ulva anandii, Ulva angusta, Ulva arasakii, Ulva armoricana, Ulva atroviridis, Ulva attenuata, Ulva beytensis, Ulva bifrons, Ulva brevistipitata, Ulva bulbosa, Ulva burmanica, Ulva byssoides, Ulva californica, Ulva chaetomorphoides, Ulva clathrata, Ulva coccinea, Ulva compressa, Ulva conglobata, Ulva cornucopiae, Ulva cornuta, Ulva covelongensis, Ulva crassa, Ulva crassimembrana, Ulva curvata, Ulva dactylifera, Ulva denticulata, Ulva elegans, Ulva elminthoides, Ulva enteromorpha, Ulva erecta, Ulva expansa, Ulva fasciata, Ulva fenestrata, Ulva flexuosa, Ulva gelatinosa, Ulva geminoidea, Ulva gigantea, Ulva grandis, Ulva hendayensis, Ulva hookeriana, Ulva hopkirkii, Ulva indica, Ulva intestinalis, Ulva intestinaloides, Ulva intricata, Ulva intybacea, Ulva javanica, Ulva kylinii, Ulva lactuca, Ulva lactucaefolia, Ulva laetevirens, Ulva laingii, Ulva linearis, Ulva lingulata, Ulva linkiana, Ulva lima, Ulva lippii, Ulva litoralis, Ulva littorea, Ulva lobata, Ulvalubrica, Ulva marginata, Ulva micrococca, Ulva myriotrema, Ulva neapolitana, Ulva nematoidea, Ulva ohnoi, Ulva olivacea, Ulva olivaceum, Ulva pacifica, Ulva papenfussii, Ulva paradoxa, Ulva parva, Ulva parvula, Ulva patengensis, Ulva percursa, Ulva pertusa, Ulva phyllosa, Ulva popenguinensis, Ulva porrifolia, Ulva procera, Ulva profunda, Ulva prolifera, Ulva pseudocurvata, Ulva pseudolinza, Ulva pulchra, Ulva purpurascens, Ulva quilonensis, Ulva radiata, Ulva ralfsii, Ulva ranunculata, Ulva reticulata, Ulva rhacodes, Ulva rigida, Ulva rotundata, Ulva rubens, Ulva saifullahii, Ulva scagelii, Ulva scandinavica, Ulva sericea, Ulva serrata, Ulva simplex, Ulva sorensenii, Ulva spinulosa, Ulva stenophylla, Ulva stipitata, Ulva sublittoralis, Ulva subulata, Ulva taeniata, Ulva tenera, Ulva tetragona, Ulva torta, Ulva tuberosa, Ulva umbilicata, Ulva uncialis, Ulva uncinata, Ulva usneoides, Ulva utricularis, Ulva utriculosa, Ulva uvoides, Ulva ventricosa.*

The extract of algae mentioned here above comprises sulfated and non-sulfated polyanionic polysaccharides the molecular weight of which is less than or equal to 50 kDa. More particularly, the algal extract comprises sulfated and non-sulfated polyanionic polysaccharides with molecular weight equal to or less than 50 kDa, whereof the molecular weight is less than 40, 30, 20 or 15 kDa. More particularly indeed, the sulfated and non-sulfated polyanionic polysaccharides of the algal extract have a molecular weight that is less than or equal to 15 kDa. Preferably, the sulfated and non-sulfated polyanionic polysaccharides of the algal extract have a molecular weight that is greater than 500 Da, preferably greater than 750 Da.

According to one embodiment of the invention, the algal extract does not comprise sulfated or non-sulfated polyanionic polysaccharides having molecular weight greater than 50 kDa (or greater than 40, 30, 20 or 15 kDa when the sulfated and not sulfated polysaccharides are defined by a molecular weight that is less than 40, 30, 20 or 15 kDa, respectively). Thus, according to one embodiment, when the algal extract comprises sulphated and non-sulphated polyanionic polysaccharides with a molecular weight that is less than or equal to 15 kDa, the algal extract does not comprise sulphated and non-sulphated polyanionic polysaccharides with a molecular weight that is greater 15 kDa.

A dalton (Da) is a unit of mass defined as being equal to one twelfth of the mass of an unbound carbon-12 atom, a mass which will subsequently be shown to be estimated from a mixture of several isotopes (mainly carbon-12 and carbon-13, having 6 and 7 neutrons respectively in addition to the 6 protons of any carbon atom). A dalton is, with a fairly good degree of precision, the mass of a hydrogen atom, the exact value being 1.00794 amu (atomic mass unit). The unit kilodalton (kDa) is equal to 1000 Da. In the context of the present invention, the masses mentioned in kDa are determined by any appropriate method usually used by the person skilled in the art, in particular the masses of sulfated and non-sulfated polyanionic polysaccharides of the algal extracts can be selectively separated by ultrafiltration on membranes that allow only molecules of predetermined sizes to filter through.

According to one embodiment, the sulfated and non-sulfated polyanionic polysaccharides having a molecular weight that is less than 50 kDa, as described here above, have a degree of polymerisation greater than 5-ose units.

In the algal extract as defined here above, the polysaccharides include mannose and/or arabinose, preferably mannose. More particularly still, the algal extract comprises at least 0.005% of mannose and/or at least 0.005% of arabinose, by weight relative to the weight of the total dry matter of the algal extract, in particular at least 0.01% of mannose and/or at least 0.01% of arabinose. Preferably, the algal extract comprises at least 0.005% of mannose.

Even more particularly, the algal extract comprises mannose in an amount ranging from 0.005 to 0.5%, for example from 0.005 to 0.2%, or from 0.15 to 0.5%; and/or arabinose in an amount ranging from 0.005 to 0.5%, by weight relative to the weight of the total dry matter of the algal extract; preferably mannose in an amount ranging from 0.005 to 0.5%, for example from 0.005 to 0.2% or 0.15 to 0.5%, by weight relative to the weight of the total dry matter of the algal extract.

Even more particularly, the algal extract comprises mannose in an amount ranging from 0.01 to 0.5%, for example from 0.01 to 0.2%, or from 0.2 to 0.5%; and/or arabinose in an amount ranging from 0.01 to 0.5%, by weight relative to the weight of the total dry matter of the algal extract; in particular mannose in an amount ranging from 0.03 to 0.45%, for example from 0.03 to 0.15%, or from 0.15 to 0.45%; and/or arabinose in an amount ranging from 0.01 to 0.2%.

Preferably, the algal extract comprises mannose in an amount ranging from 0.01 to 0.50%, for example from 0.01 to 0.20%, or from 0.20 to 0.5%, in particular mannose in an amount ranging from 0.03 to 0.45%, for example from 0.03 to 0.15%, or from 0.15 to 0.45%, by weight relative to the weight of the total dry matter of the algal extract.

According to one embodiment, the algal extract comprises:
    galactose; and/or
    glucose; and/or
    rhamnose; and/or
    xylose; and/or
    glucuronic acid.

More particularly, the algal extract comprises:
    from 0.05 to 0.5% of galactose, in particular from 0.1 to 0.4%; and/or
    from 0.005 to 0.5% of glucose, in particular from 0.005 to 0.05% in particular from 0.01 to 0.03%, or from 0.05 to 0.5%; and/or
    from 2 to 15% of rhamnose, in particular from 5 to 10%; and/or
    from 0.1 to 1% of xylose, in particular from 0.3 to 0.7%; and/or
    from 1 to 7% of glucuronic acid, in particular from 1 to 5%;
    by weight relative to the weight of the total dry matter of the algal extract.

Thus, according to one embodiment, the algal extract comprises:
    mannose; and/or
    arabinose; and/or
    galactose; and/or
    glucose; and/or
    rhamnose; and/or
    xylose; and/or
    glucuronic acid.

Mention may more particularly be made, for example, of the algal extract comprising:
    from 0.01 to 0.5% of mannose, for example from 0.01 to 0.2%, in particular from 0.03 to 0.15%, or from 0.2 to 0.5%; and/or
    from 0.01 to 0.5% arabinose, in particular from 0.01 to 0.2%; and/or
    from 0.05 to 0.5% of galactose, in particular from 0.1 to 0.4%; and/or
    from 0.005 to 0.5% of glucose, in particular from 0.005 to 0.05%, in particular from 0.01 to 0.03%, or from 0.05 to 0.5%; and/or
    from 2 to 15% of rhamnose, in particular from 5 to 10%; and/or
    from 0.1 to 1% of xylose, in particular from 0.3 to 0.7%; and/or
    from 1 to 7% of glucuronic acid, in particular from 1 to 5%;
    by weight relative to the weight of the total dry matter of the algal extract.

Indeed even more particularly, mention may be made, for example, of the algal extract comprising:
    0.09% mannose; and/or
    0.1% arabinose; and/or
    0.3% galactose; and/or
    0.02% glucose; and/or
    8.1% rhamnose; and/or
    0.5% xylose; and/or
    2.6% glucuronic acid;
    by weight relative to the weight of the total dry matter of the algal extract.

Mention may also be made, for example, of the algal extract comprising:
    0.3% mannose; and/or
    0.2% galactose; and/or
    0.4% glucose; and/or
    7.9% rhamnose; and/or
    0.5% xylose; and/or
    4.9% glucuronic acid;
    by weight relative to the weight of the total dry matter of the algal extract.

According to one embodiment, the algal extract comprising sulfated and non-sulfated polyanionic polysaccharides having a molecular weight that is less than or equal to 50 kDa, as described here above, comprises:
    from 10 to 50% carbon;
    from 1 to 10% hydrogen;
    from 1 to 5% nitrogen;
    from 20 to 50% oxygen; and
    from 1 to 15% sulfur;
as a percentage by mass of the total dry matter of the algal extract.

Indeed even more particularly, the algal extract comprises:
    from 15 to 30% carbon;
    from 3 to 6% hydrogen;
    from 1 to 3% nitrogen;
    from 25 to 40% oxygen; and
    from 2.5 to 10% sulfur;
as a percentage by mass of the total dry matter of the algal extract.

According to one other embodiment of the invention, the algal extract comprises:
    from 10 to 50% of carbon;
    from 1 to 10% hydrogen;

from 0.5 to 5% nitrogen;
from 20 to 60% oxygen; and
from 1 to 15% sulfur;
as a percentage by mass of the total dry matter of the algal extract.

The other chemical elements present in the dry matter of the extract are in particular represented by the minerals (Ca, K, Na, Mg, Al, Cl, I, P, Fe, etc.).

More particularly, the algal extract as described in the context of the present invention is characterised by the $^1$H NMR spectrum presented in FIG. 1.

This $^1$H NMR spectrum was recorded at 298 K on a Bruker Avance 500 spectrometer equipped with a 5 mm inverse TCI cryogenic probe $^1$H/$^{13}$C/$^{15}$N. Prior to the analysis, the samples were dissolved in 99.97% of D20. The chemical shifts are expressed in ppm relative to an external standard (trimethylsilyl propionic acid). No HOD signal suppression was performed.

The algal extract of the order Ulvales comprising sulfated and non-sulfated polyanionic polysaccharides having a molecular weight that is less than or equal to 50 kDa, as described here above, is capable of being obtained, or is obtained, by means of a method of preparation in which:
a) the algae are washed and desanded;
b) the said algae are ground;
c) the solid phase of the ground material is separated from its liquid phase;
d) the said liquid phase is clarified;
e) the juice obtained in step d) is ultra filtered through a membrane having pore size of 50 kDa or less; and
f) the filtration juice obtained in step e) is concentrated and then dried.

According to one embodiment, the method of preparation in addition includes a step of freezing followed by a thawing process, between the step a) of washing/desanding and the step b) of grinding.

In particular, for the implementation of the method as indicated in the context of the present invention, in step a) thereof, the algae are washed with fresh water.

They may be desanded by any means that are available to the person skilled in the art.

The said algae are then ground, in particular by means of a grinder, such as for example a refiner or a cutter.

Thereafter, the solid phase of the ground material, the marc, is separated from its liquid phase, the juice, by pressing the ground material, for example using a belt or plate press, or by centrifugation.

The term "juice" is understood to refer to the cytoplasmic juice which includes the parietal structure of the double-membrane structure of algae cells.

The liquid phase obtained is then clarified, for example with a disc stack clarifier, or by centrifugation, decantation or filtration (for example with bag or plate filters).

The juice obtained is then ultra filtered.

According to one embodiment for implementing the method as indicated in the context of the present invention, the ultrafiltration is carried out on a membrane having pore size (or nominal molecular weight limit NMWL) of 50 kDa or less, in particular on a membrane having pore size of 40, 30, 20 or 15 kDa. More particularly, the membrane is a membrane having pore size of 15 kDa or less.

This membrane can for example be a ceramic membrane or an organic membrane. More particularly, the membrane is a ceramic membrane.

The filtration juice obtained can thereafter be concentrated, for example by reverse osmosis, evaporation or precipitation, and then dried for example by lyophilisation or atomisation.

Optionally, the concentration step may be preceded by a demineralisation step, in particular on a membrane having a size between 150 and 1000 Da.

Optionally, the extract obtained could then be ground again, in order to obtain a powder that is homogeneous in terms of particle size.

According to one of these aspects, the method is carried out in part at ambient temperature. The term "ambient temperature" is understood to indicate a temperature between 5 and 25° C.

According to another of these aspects, the method is carried out in part at a temperature of between 4 and 10° C., this being in order to prevent microbial development and growth.

According to one embodiment for implementing the method as indicated in the context of the present invention, the algal extract obtained in step f) of the above-mentioned method is purified, for example by ultrafiltration, in particular on an ultrafiltration cassette, in particular in order to remove the mineral part. According to an alternative embodiment, this purification may also be carried out before the concentration step f) or during the concentration step f).

The preparation method for preparing the algal extract as described here above does not use solvents, in particular organic solvents, and more particularly solvents other than water.

Preferably, the algal extract of the order Ulvales comprising sulfated and non-sulfated polyanionic polysaccharides having molecular weight less than or equal to 50 kDa exhibits one or more of the following effects:
it limits systemic bacterial spread, preferably by a mechanism mediated by NK cells;
it increases the number of total NK cells and the number of INFγ producing NK cells, preferably without increasing the percentage of INFγ$^+$ NK cells, at the site of the infection;
it does not increase the proportion of pro-inflammatory cytokines-producing innate immune cells at the site of the infection (in particular IL-12 producing DCs and/or TNFα-producing macrophages and/or INFγ producing NKs or TLs);
it has no direct antibacterial effect, in particular on methicillin-suscitible *Staphylococcus aureus;*
it does not induce an increase in the production of interferon γ by NK cells, by direct stimulation in vitro;
it does not induce an increase in the expression of the marker KLRG1 in NK cells, by direct stimulation in vitro;
it does not induce an increase in the level of chemokine CXCL-1 and/or CXCL-2 at the site of the infection.

Pharmaceutical Composition

The algal extract of the order Ulvales comprising sulfated and non-sulfated polyanionic polysaccharides having molecular weight less than or equal to 50 kDa is preferably formulated in a pharmaceutical composition or a medicament.

A pharmaceutical composition or medicament for the implementation of the invention typically includes the algal extract of the order Ulvales comprising sulfated and non-sulfated polyanionic polysaccharides having molecular weight less than or equal to 50 kDa, and a pharmaceutically acceptable excipient.

The pharmaceutically acceptable excipients used for the preparation of a medicament or a pharmaceutical composition comprising an algal extract for use thereof according to the invention are selected based on the pharmaceutical form and the desired mode of administration, from among the usual excipients which are known to the person skilled in the art.

For oral, sublingual, subcutaneous, intramuscular, intravenous, topical, local, intraperitoneal, intratracheal, intranasal, transdermal or rectal administration, the algal extract as defined here above may be administered in the form of unit doses, in admixture with conventional pharmaceutical excipients.

The appropriate forms for administration include oral route forms such as tablets, soft or hard capsules, powders, granules, and oral solutions or suspensions; forms for sublingual, buccal, intratracheal, intraocular, intranasal administration, and administration by inhalation; forms for topical, parenteral administration such as transdermal, intraperitoneal, intratracheal, subcutaneous, intramuscular or intravenous; forms for rectal administration, and implants.

When a solid composition in the form of tablets is prepared, the main active ingredient can be in admixture with a pharmaceutical carrier, such as gelatin, starch, lactose, magnesium stearate, talc, arabic gum, or the like.

The tablets may also be coated with saccharose, a cellulose derivative, or other appropriate materials or indeed they may be appropriately treated so as to ensure that they have a prolonged or delayed activity and that they continuously release a predetermined quantity of active ingredient.

A preparation in the form of capsules can for example be obtained by admixing the active ingredient with a diluent and by pouring the mixture obtained into soft or hard capsules.

In one embodiment, the algal extract, the medicament or the pharmaceutical composition for use according to the present invention is intended for oral administration.

In one other embodiment, the algal extract, the medicament or the pharmaceutical composition for use according to the present invention is intended for parenteral administration. In one other embodiment, the algal extract, the medicament or the pharmaceutical composition for use according to the present invention is intended for intraperitoneal administration The medicaments or pharmaceutical compositions comprising an algal extract for use according to the invention may also be presented in liquid form, for example, in the form of solutions, emulsions, suspensions or syrups; and in particular in a form suitable for oral or intranasal administration, for example. Appropriate liquid carriers may be, for example, water, organic solvents such as glycerol or glycols, as well as mixtures thereof, in varying proportions, in water.

A preparation in the form of a syrup or elixir or for administration in the form of drops may also contain the active ingredient together with a sweetener, having no- or low-calories for example, methylparaben and propylparaben as an antiseptic, as well as a flavouring agent and an appropriate colouring agent.

The powders or granules that are water-dispersible may for example contain the active ingredient in admixture with dispersing agents or wetting agents, or suspending agents, such as polyvinylpyrrolidone, as well as with sweeteners or flavour correctors.

In general, in the context of the present invention, the daily dose of the algal extract will be the lowest effective dose of the algal extract that is capable of producing a prophylactic and/or therapeutic effect on post-traumatic immunosuppression.

The term "effective dose" is understood to refer to any amount of a composition which makes it possible to obtain the observed desired effect, in this instance an immunostimulatory effect.

According to one of its aspects, an algal extract for use according to the invention is used in a composition as mentioned above for administration at a dose in/for humans of between 0.1 and 300 mg/kg, for example between 0.1 and 100 mg/kg, even more particularly between 0.5 and 60 mg/kg, for example between 1 and 20 mg/kg, or between 5 and 30 mg/kg, or at a dose in animals of between 1 and 300 mg/kg, or between 1 and 200 mg/kg, more particularly between 1 and 100 mg/kg, indeed even more particularly between 2 and 45 mg/kg, or between 10 and 60 mg/kg.

According to one of its aspects, an algal extract for use according to the invention is used in a composition as mentioned above for administration via the oral route at a dose in humans of between 100 and 300 mg/kg, for example between 50 and 100 mg/kg, or at a dose in animals of between 100 and 300 mg/kg, or between 100 and 200 mg/kg.

Prophylactic or Therapeutic Treatment of Complications Induced by Post-Traumatic Immunosuppression In the context of the invention, the terms "treat" or "treatment" are understood to refer to suppressing, alleviating or preventing the progression of a disorder or of one or more symptoms related to this disorder. A "prophylactic" or "preventive" treatment pertains to preventing the occurrence of such a disorder or one or more symptoms related to this disorder.

A subject for the prophylactic or therapeutic treatment according to the invention is an animal, preferably a mammal, for example a rodent, a canine, a feline, a bovine, an equine, or a primate. A subject is in particular a human, whether man, woman or child.

The subject presents with a post-traumatic immunosuppression. Generally a post-traumatic immunosuppression occurs as a consequence of one or more severe traumas in the subject, such as a cranial trauma, in particular a cranial trauma with or without polytrauma (multiple trauma), major surgery or a severe infection.

According to one embodiment, the subject in question with severe trauma presents at least two traumatic injuries (polytrauma (multiple trauma)) of which at least one injury is life-threatening. The subject is generally hospitalised, for example in a hospital intensive care unit. The subject may more particularly be placed under artificial ventilation, in particular with intubation.

According to one embodiment, the subject with severe trauma has an "Injury Severity Score" (or ISS) of at least 16. For very severe trauma, the ISS is at least 25. The calculation of the ISS takes into account the damage caused to several regions of the patient's body (head and neck; face; thorax; abdomen and pelvis; pelvic girdle and limbs; skin and subcutaneous tissue). The damage to each region is rated from 1 to 6 depending on its severity (1: minor impairment, 6: critical impairment). The ISS is then calculated by squaring the score of the three most impaired regions (for example, if the ratings for each region are respectively as follows: head 4, abdomen 3, thorax 2, other regions 1, then the ISS will be will amount to $4^2+3^2+2^2=16+9+4=29$ (Baker et al., 1974, J Trauma. 14: 187-196).

According to one embodiment, the subject with severe trauma presents a severe cranial trauma defined by a Glasgow Coma Scale (GCS) score of less than 8. The determination of the GCS is a method which provides the means to assess the depth of a coma by studying the variability of 3 very precise clinical criteria as follows: 1) opening of the eyes (rated from 1: 'no eye opening' to 4: 'eyes opening spontaneously'); 2) motility capacity (ability to move), or as may be preferred, the best motor response (rated from 1: 'no motor response' to 6: 'obeys commands'); and 3) response to the questions posed (verbal responses, rated from 1: 'no verbal response' to 5: 'oriented response'). The GCS is the sum of the results obtained with the three clinical criteria mentioned above. Therefore the scores range from a minimum of 3 to a maximum of 15 (Teasdale et al. 1974, Lancet 2: 81-84).

The post-traumatic immunosuppression is preferably characterised by:

a) a drop in the level of ex vivo production of pro-inflammatory cytokines induced by blood leukocytes after stimulation with LPS of Gram-negative bacilli, for example *Escherichia coli*, as compared to the level of production observed for a healthy individual; and/or b) a drop in the level of HLA-DR (Human Leukocyte Antigen—DR isotype) expression on the patient's antigen presenting cells, as compared to the level of expression observed for a healthy individual.

The observed decrease in the level of production of cytokines (expressed for example in picogrammes/ml) is reported against healthy volunteers whose level of cytokine production represents the value 100%. The cytokines are typically measured in whole blood cultures stimulated by LPS (from *Escherichia coli* in general). The expression of HLA-DR is reported against healthy volunteers, either in number of HLA-DR molecules expressed on the surface of the cells (MFI for "mean fluorescence intensity"), or in percentage terms, the value 100% representing the level of HLA-DR expression in healthy volunteers. In particular, if taken into account in percentage terms, the drop in a) and/or b) above is at least approximately 20%. It is preferably at least approximately 25%, more preferably at least approximately 30, 35, 40, 45%, and more preferentially at least approximately 50, 55, 60%, or even more.

More preferably, the post-traumatic immunosuppression observed in the patient with severe trauma is such that the level of HLA-DR expression on the monocytes of the said patient within 24 hours following the one or more trauma(s) (from D0 to D1) is reduced as compared to the level of expression observed for a healthy individual. This initial reduction can moreover make it possible, in practice, to predict the risk of septic complications (or secondary infections). Thus, a low level of HLA-DR expression on monocytes on the first day following the one or more severe trauma(s) (D1), for example a reduction of 50%, is predictive of a high risk for the patient of contracting a secondary infection. The expression of HLA-DR is reported against healthy volunteers, either in number of HLA-DR molecules expressed on the surface of the cells (MFI for "mean fluorescence intensity"), or in percentage terms, the value 100% representing the level of HLA-DR expression in healthy volunteers. In particular, if taken into account in percentage terms, the decrease in the level of HLA-DR expression is at least approximately 20%, preferably at least approximately 25%, more preferably at least approximately 30, 35, 40, 45%, and more preferentially at least approximately 50, 55, 60%, or even more.

According to one embodiment, the prevention and/or treatment of post-traumatic immunosuppression leads to the prevention and/or treatment of a septic complication associated with post-traumatic immunosuppression.

The septic complications (or secondary infections) associated with post-traumatic immunosuppression are more particularly nosocomial infections, in particular bacterial or fungal or viral infections. In particular, the nosocomial infections in question are selected from the group consisting of pneumopathies, such as pneumonia acquired under mechanical ventilation, ie ventilator-associated pneumonia (VAPs), urinary tract infections, infections of central venous catheters, bacterial cerebromeningeal infections such as empyema, meningitis and brain abscess. More particularly still, the pneumopathies are due to pathogenic bacteria selected from among staphylococci, preferably *Staphylococcus aureus*, more preferably methicillin-suscitible *Staphyloccocus aureus, Haemophilus* sp., preferably *H. influenza*; pneumococci; enterobacteria, *Pseudomonas* sp., in particular *P. aeruginosa*. The bacteria causing the pneumopathies may also belong to other bacterial genera or species (for example, Gram-negative bacilli and Gram-positive cocci). In addition, they may be resistant to antibiotics. In the case of infections other than pneumopathies, the bacteria or yeasts responsible may be, for example, Gram negative bacilli (eg, *E. coli, Proteus mirabilis, Pseudomonas aeruginosa*) and Gram positive cocci (eg, *S. aureus*) for urinary tract infections; Gram-negative bacilli (eg, *E. coli, P. mirabilis, P. aeruginosa*), Gram-positive cocci (eg, *S. aureus*, coagulase-negative staphylococci) and yeasts such as *Candida* sp. for infections of central catheters; Gram-negative bacilli (eg, *E. coli, P. mirabilis, P. aeruginosa*) and Gram-positive cocci (eg, *S. aureus*, coagulase negative staphylococci, *Streptococcus pneumoniae*) for bacterial cerebromeningeal infections.

According to one embodiment, the site of infection (or point of origin of infection) is the lung.

The algal extract, or the composition or the medicament containing it, is preferably administered, one or more times if necessary, within a period of at most about 1 month, preferably at most 28 days, as from the date of admission of the patients to the hospital, in particular in a hospital intensive care unit. In other words, the septic complications that it is sought to prevent are likely to occur (or be contracted) over a period of at most about 1 month, preferably at most 28 days, as from the date of admission of the patients to the hospital. For example, it was found that the septic complications occurred in 40 to 50% of the severe trauma patients between D0 and D10, and in 10 to 20% of additional patients between D10 and D28, that is to say 50 to 70% of patients in total had contracted a secondary infection (Osborn et al., 2004 Crit. Care Med.; 32 (11): 2234-40).

In particular, the algal extract, or the composition or the medicament containing it, is administered one or more times during the period of intubation of the patients.

In the present application, the term "and/or" is a grammatical conjunction which is to be interpreted as encompassing the fact that one or more of the cases or instances that it connects may occur. For example, the expression "mannose and/or arabinose" in the expression "the said polysaccharides include mannose and/or arabinose" indicates that the polysaccharides may include mannose, or arabinose, or mannose and arabinose.

Throughout the present patent application, the term "comprising" should be interpreted to include all of the characteristic features specifically mentioned, as well as optional, additional, unspecified characteristics. As used herein, the use of the term "comprising" also describes embodiments in which no characteristic other than the characteristic features specifically mentioned is present (that is to say "consisting of").

The present invention will be illustrated in greater detail by the figures and examples below without however limiting the scope thereof.

FIGURES

FIG. 1: Diagram schematically representing the experimental protocol for the bacteriological analyses.

Figure 2:
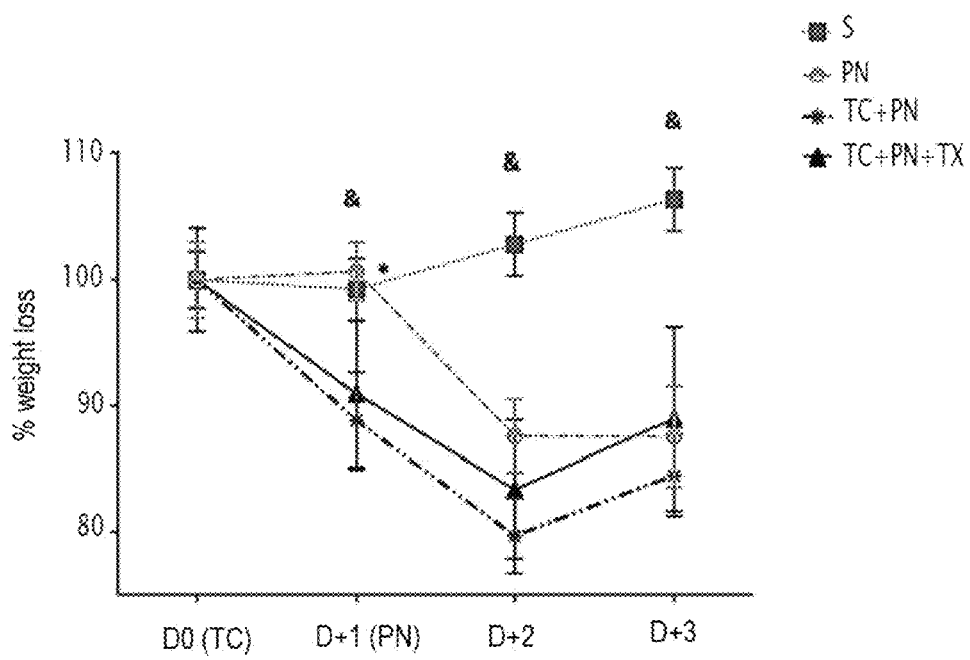

FIG. 2: The algal extract has no effect on the weight loss of trauma subjected and secondarily infected mice. The mice in the Sham (S) and Pneumonia alone (PN) groups received the 1 cm incision on the skull without cranial trauma (TC). The trauma subjected and infected mice, for whom the pneumonia was induced 24 hours after subjecting to TC, were divided into the group not treated (TC+PN) and the group treated with 6 injections of the compound (every 12 hours starting from TC until euthanasia) (TC+PN+TX). The pneumonia was induced 24 hours after subjecting to TC with the mice being euthanised 48 hours after the pneumonia. The results are derived from 2 independent experiments (each group n=9). The % weight loss results are provided as means±standard deviation. *$p<0.05$ trauma subjected and PN groups (after PN) versus S, *$p<0.05$ for trauma subjected groups versus PN.

Figure 3:
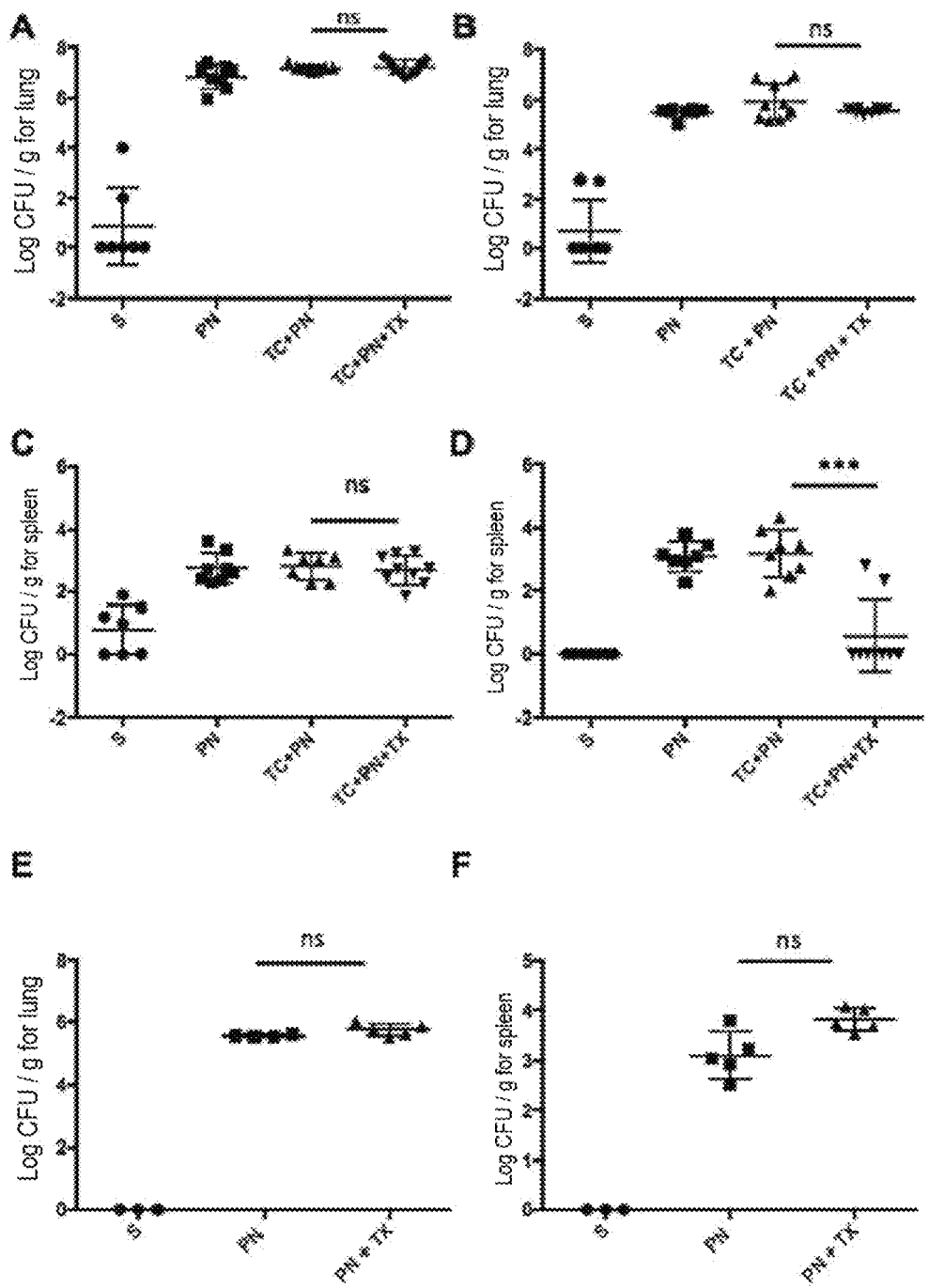

FIG. 3: The algal extract limits the splenic spread of bacteria in trauma subjected mice after induction of MSSA pneumonia but has no effect in the absence of trauma: The mice of the Sham (S) and Pneumonia alone (PN) groups received the 1 cm incision on the skull without TC. The trauma subjected and infected mice were divided into the group not treated (TC+PN) and the group treated with the compound (200 µg every 12 hours, starting from TC until euthanasia) (TC+PN+TX). The lungs were removed 24 hrs (A) and 48 hrs (B) after the induction of pneumonia. The spleens were removed 24 hrs (C) and 48 h (D) after induction of pneumonia. The ground organs cultured on Chapman agar media were incubated for 24 hrs and thereafter the colonies were counted. The results derived from 2 independent experiments (n=8 or 9 per group) and are provided as mean $Log_{10}$ CFU (colony-forming unit)±standard deviation. ***$p<0.001$. (E) and (F): The mice were divided into 3 groups: Sham (S); pneumonia not treated (PN); and pneumonia treated with algal extract every 12 hours for 48 hours (without trauma) (PN+TX). The lungs (E) and spleens (F) were removed 48 hours after the induction of pneumonia. The results are from one experiment (n=5 per group of interest). The results are provided as mean±standard deviation.

Figure 4:
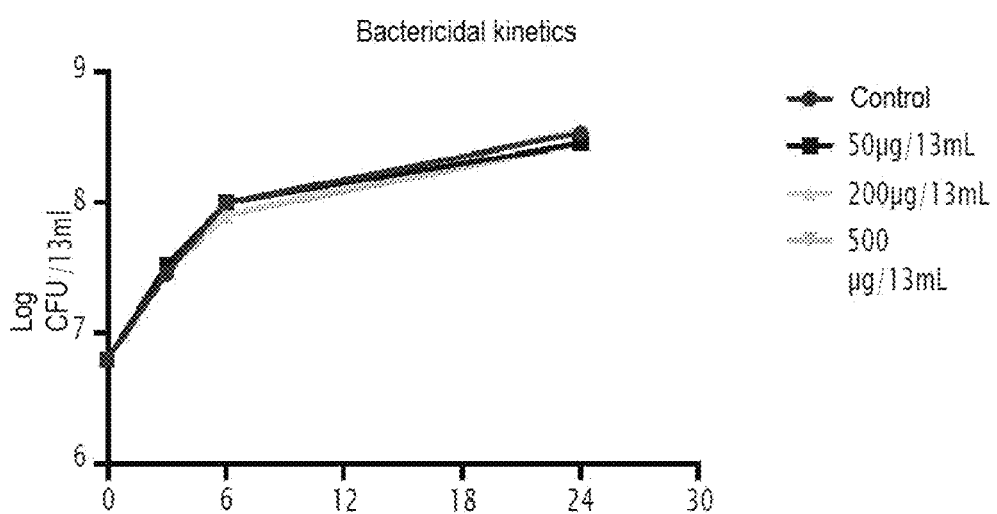

FIG. 4: The algal extract does not have anti-MSSA activity in vitro. The kinetics of bactericidal activity were developed/determined in a liquid medium for concentration ranges of 50, 200 and 500 µg/ml of the compound. The bacterial loads were then counted on TS agars and the results expressed in $Log_{10}$ CFU/mL. The results are from 2 independent and consistent experiments.

FIG. 5: Intraperitoneal administration of the algal extract does not induce an increase in secretion of pro-inflammatory cytokines at 2 hours in naive mice. The intraperitoneal injection of the algal extract was carried out at 3 concentrations (50, 200 and 500 µg) and was compared with the injection of phosphate-buffered saline PBS (Sham) and with 1 mg/kg of LPS. The secretions of IL-12 by pulmonary DCs (FIG. 5A), TNFα by alveolar macrophages (FIG. 5B) and interstitial macrophages, as well as of INF γ by pulmonary NKs (FIG. 5C) and TLs were evaluated by flow cytometry after intracellular staining. No difference was found in the spleen (data not shown). The results are from one experiment (n=2 per group) and are provided as a median±interquartile ranges.

Figure 6:
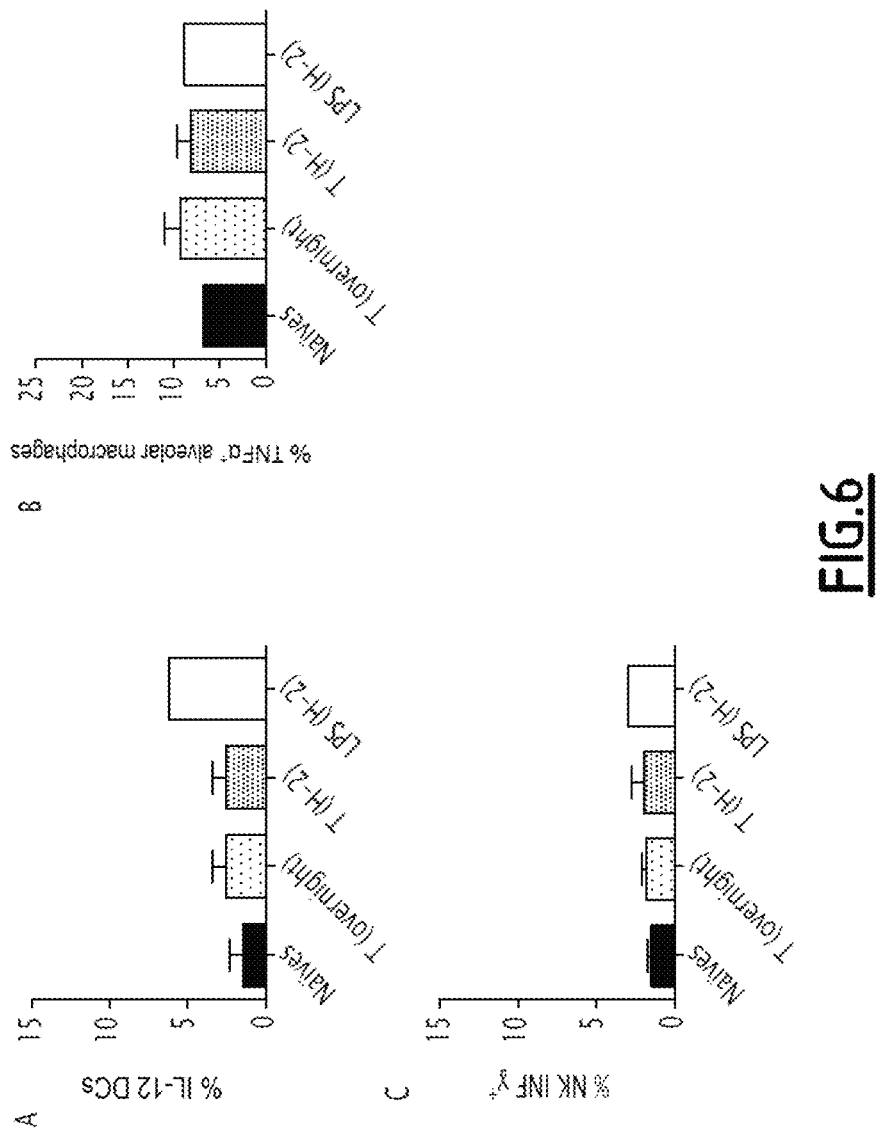

FIG. 6: Intratracheal administration of the algal extract does not induce an increase in secretion of pro-inflammatory cytokines at 2 hours and at 12 hours in a naive mouse. The intratracheal injection of the algal extract was carried out at a concentration of 50 µg, 12 hours (T overnight) and 2 hours (T (H-2)) before euthanasia. It was compared to healthy mice (Naives) and to the instillation of 50 µg of LPS two hours before euthanasia (LPS (H-2)). The secretions of IL-12 by pulmonary DCs (FIG. 7A), TNFα by alveolar macrophages (FIG. 7B) and interstitial macrophages, as well as of INF γ by pulmonary NKs (FIG. 7C) and TLs were evaluated by flow cytometry after intracellular staining. No difference was found in the spleen (results not shown). The results are from one experiment (n=2 per group) and are provided as a median±interquartile ranges.

Figure 7:
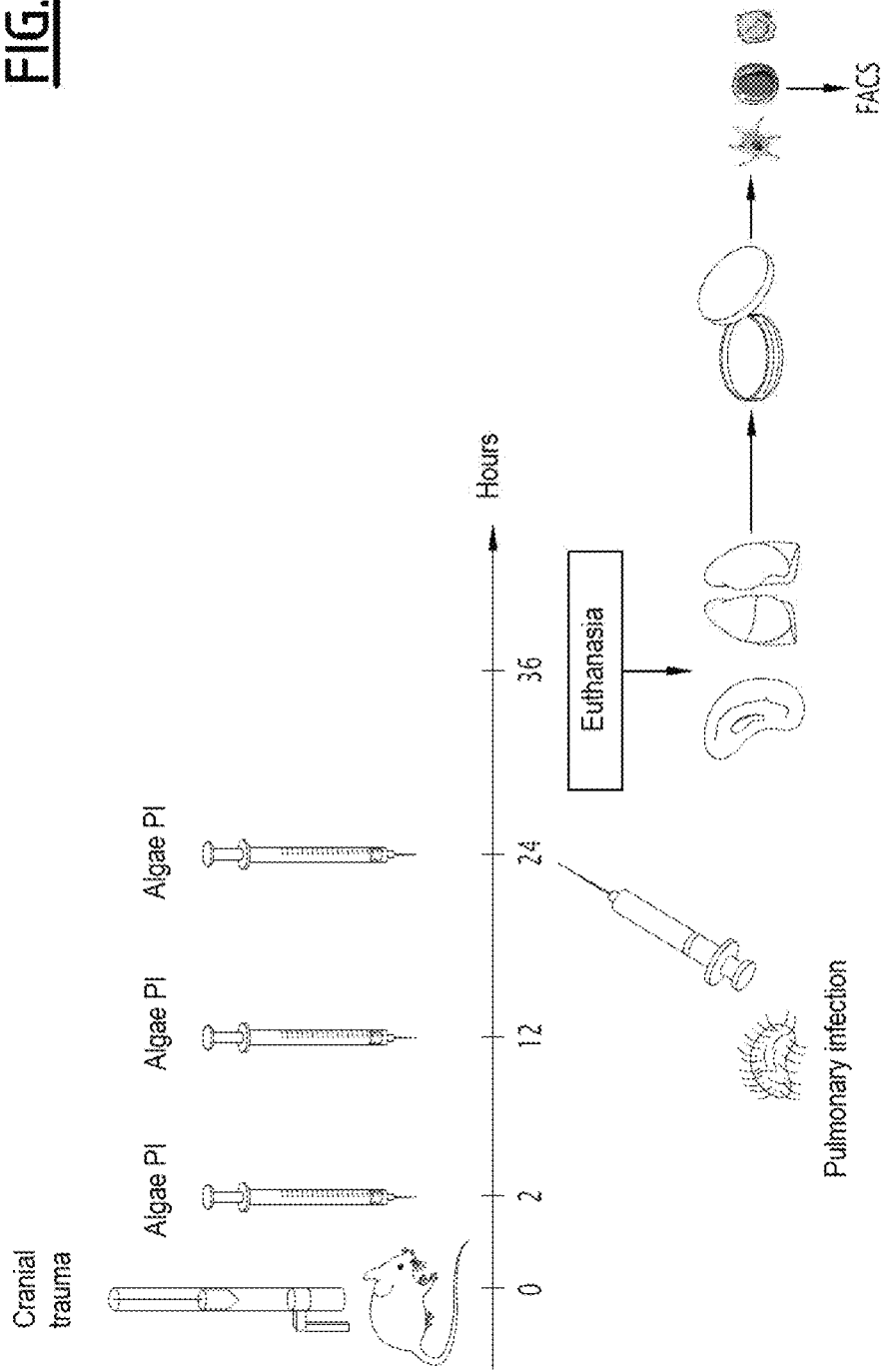

FIG. 7: Diagram schematically representing the experimental protocol for fluorescence-activated cell sorting (FACS) and enzyme linked immunosorbent assay (ELISA) analyses.

Figure 8:
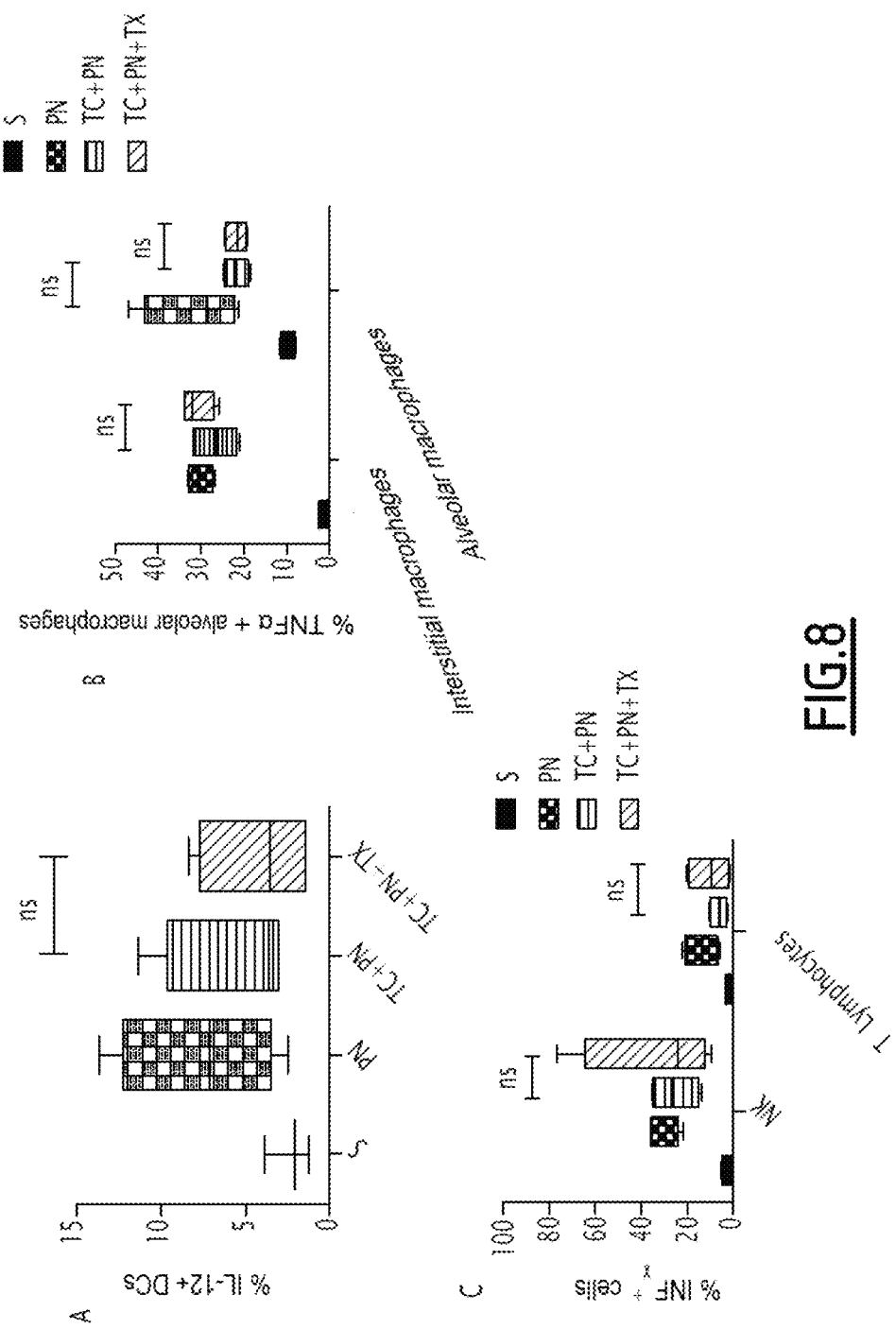

FIG. 8: Intra-peritoneal administration of the algal extract in trauma subjected mice suffering from MSSA pneumonia does not increase the proportion of cells producing pro-inflammatory cytokines in the lung.

The mice were divided into 4 groups: Sham (S); pneumonia only (PN); TC+pneumonia not treated (TC+PN); and treated with algal extract (TC+PN+TX). The pneumonia was instilled 24 after subjecting to TC with the mice being euthanised 12 hrs post pneumonia. The mice in the treated group received 3 intraperitoneal injections of 200 µg of the algal extract (every 12 hours, starting from TC until euthanasia). Secretions of IL-12 by CDs (A), TNFα by macrophages (B), and INF γ by TLs and NKs (C) were analysed by flow cytometry after intracellular staining. The results are from 2 different experiments (n=4 per group). The results are provided as the median percentage of positive cells±interquartile ranges. No difference was found in the spleen (results not shown).

Figure 9:
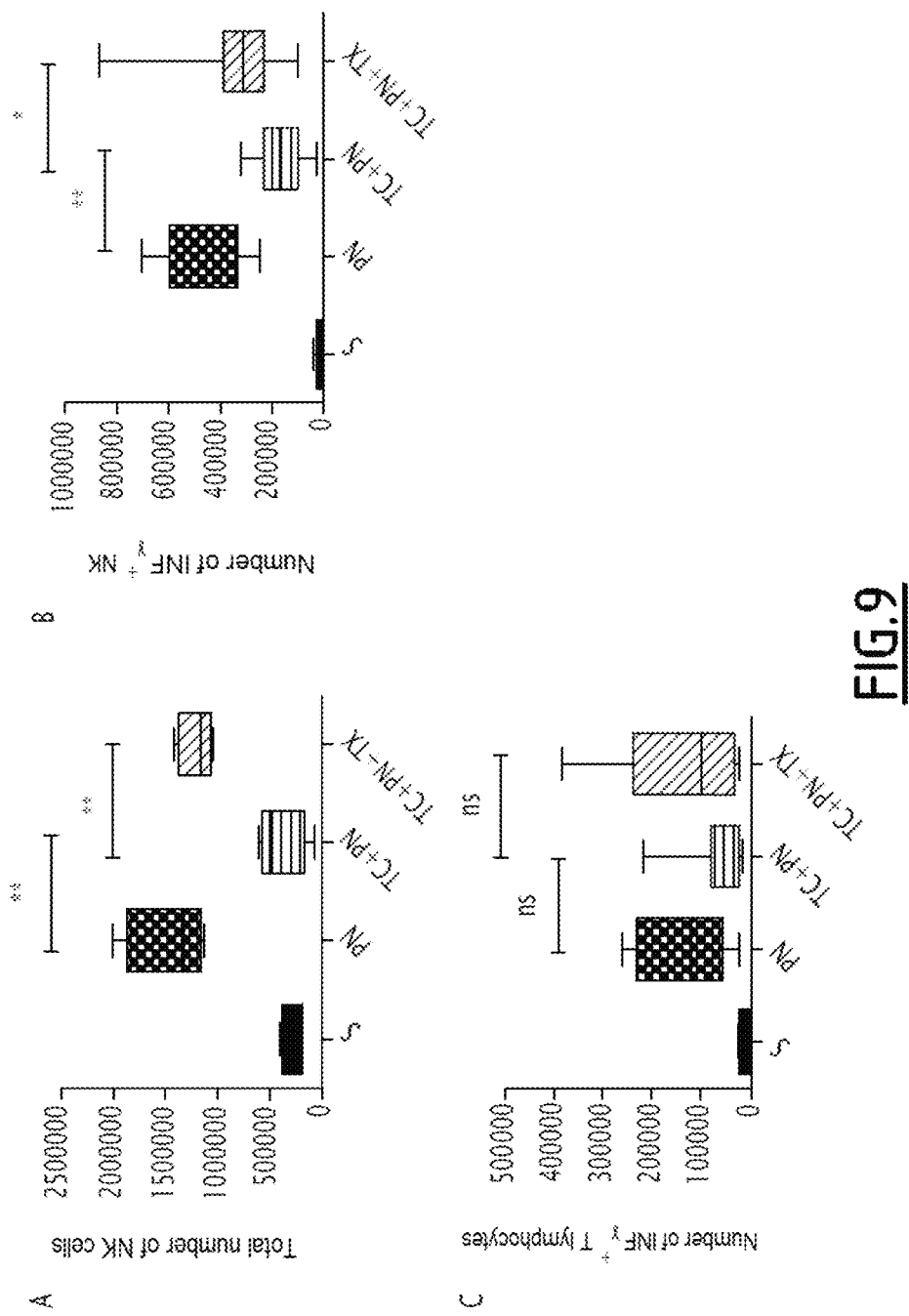

FIG. 9: Administration of the algal extract in trauma subjected, infected mice induces an increase in the number of pulmonary NK cells producing interferon γ. The mice were divided into 4 groups: Sham (S); pneumonia only (PN); cranial trauma TC+pneumonia not treated (TC+PN); and pneumonia treated with algal extract (TC+PN+TX). The pneumonia was instilled 24 hours after subjecting to TC with the mice being euthanised 12 hours post pneumonia. The mice in the treated group received 3 intraperitoneal injections of 200 µg of the algal extract (every 12 hours, starting from TC until euthanasia). The total number of NK cells (A), of interferon γ producing NK cells (B), and of interferon γ producing TLs (C) were analysed by flow cytometry after intracellular staining of cytokines. The results are from 3 independent experiments (n=9 per group). The results are provided as median±interquartile ranges. (*$p<0.05$, **$p<0.01$).

Figure 10:
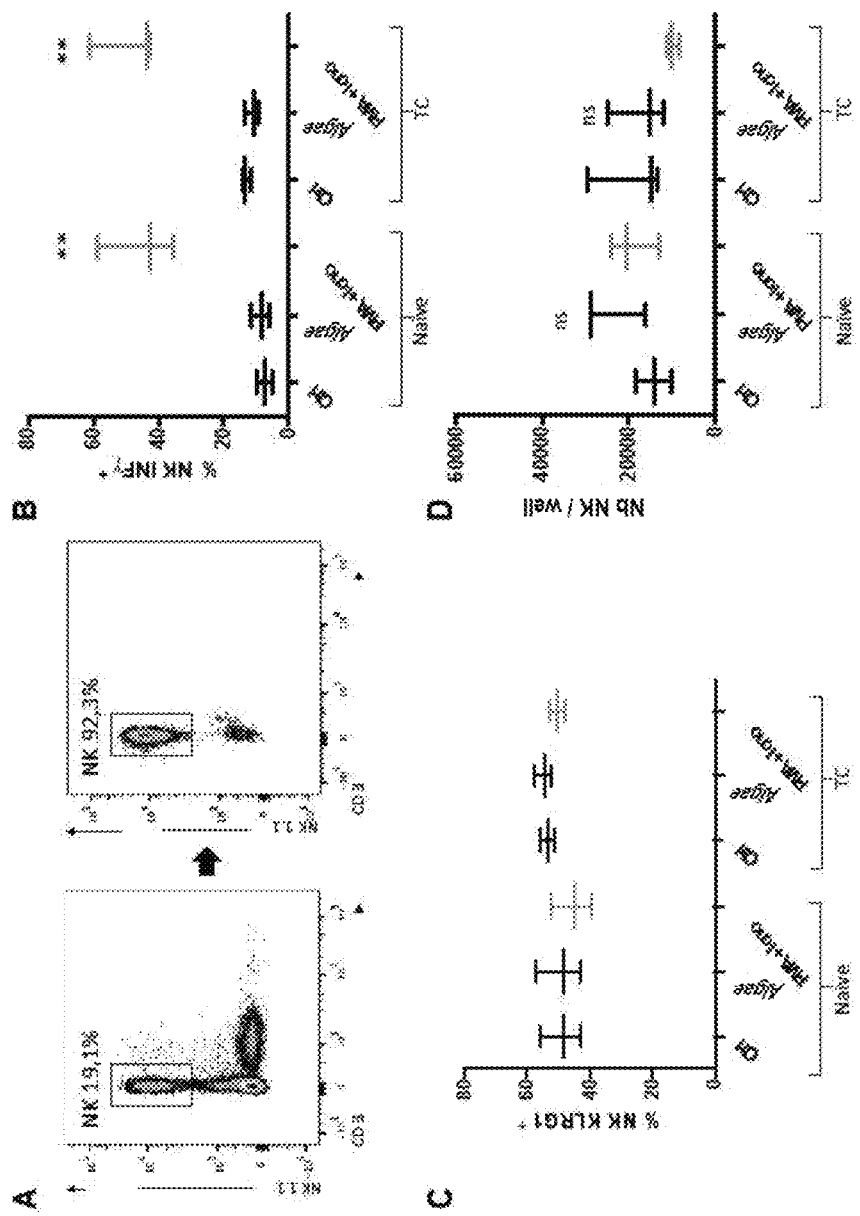

FIG. 10: The algal extract does not induce an increase in secretion of INF γ or an increase in expression of the activation factor KLRG 1 in pulmonary NK cells in vitro: The lungs of 6 naive mice and 6 trauma subjected mice were mechanically ground two at a time 24 hours after the TC in order to obtain 3 pulmonary homogenates per group. After being magnetically sorted, the NK cells were cultured for 5 hours with: IL-2 (control group: Ctrl); IL-2+Alga at 500

µg/mL (Alga); and IL-2+phorbol myristate acetate PMA (50 ng/mL) and Ionomycin (1 µg/mL) (PMA+Iono). The purity of the homogenate of NK cell was checked by flow cytometry before (A left) and after (A right) magnetic sorting. The percentage of INF γ producing NKs (B), the membrane expression of KLRG 1 (C), and the number of NKs per well after stimulation (D) were evaluated by flow cytometry. The results are from one experiment (n=3 per group) and provided as median±interquartile ranges. **$p<0.01$ as compared to the Ctrl and Alga groups. "Ns" compared to the other 2 groups.

Figure 11:
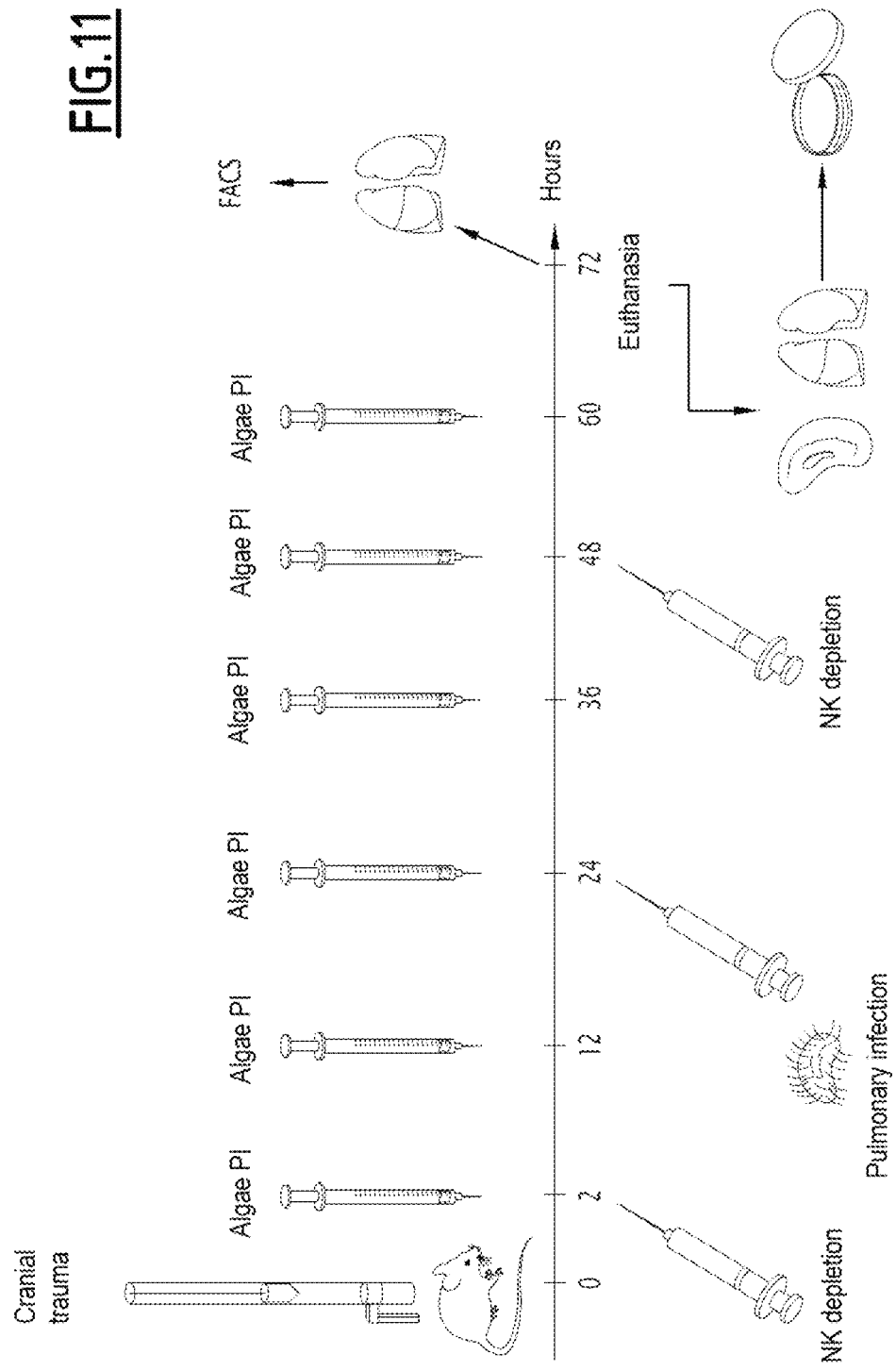

FIG. 11: Diagram schematically representing the experimental protocol for FACS and bacteriology analyses.

Figure 12:
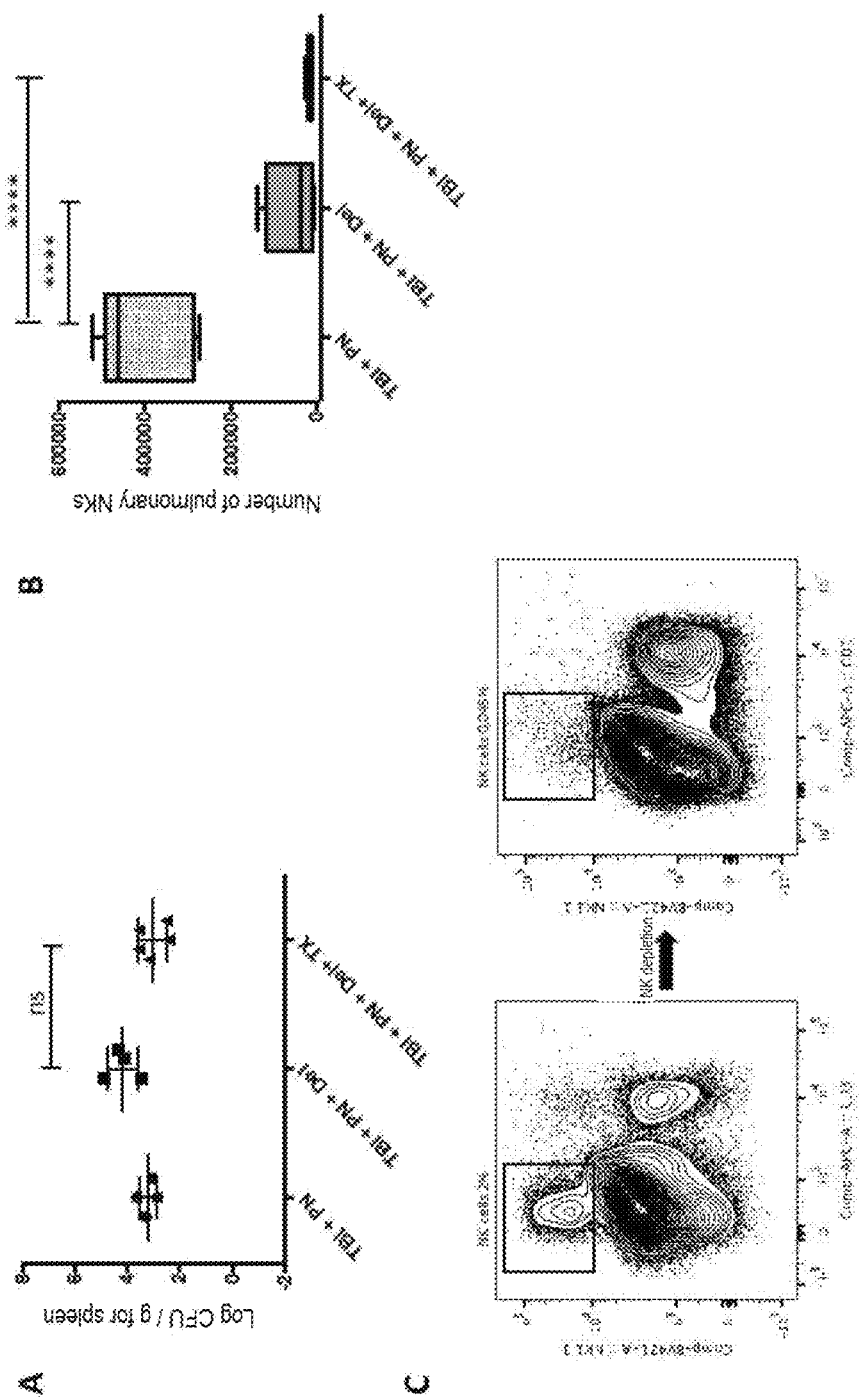

FIG. 12: Administration of the algal extract in trauma subjected, NK cell depleted mice does not limit the bacterial spread in the spleen at 48 hrs following infection. The mice were divided into 3 groups: trauma subjected and infected (TBI+PN); trauma subjected, infected and NK cell depleted (TBI+PN+del); trauma subjected, infected, NK cell depleted and treated with algal extract (TBI+PN+del+TX). The pneumonia was instilled 24 hours after TC and the NK cell depletion was brought about by IV injection of anti-NK1.1 Ab at 2 hrs and 48 hrs after TC. The mice in the treated group received 1 intraperitoneal injection of 200 µg of the algal extract every 12 hours, starting from TC until euthanasia. Euthanasia was performed at 72 hrs following the TC for FACS analysis of the splenic bacterial loads (FIG. 12 A) and the quality of pulmonary NK cell depletion (FIGS. 12B and C). The results are from one experiment (n=4 per group) and provided as median±interquartile ranges. ****$p<0.0001$.

Figure 13:
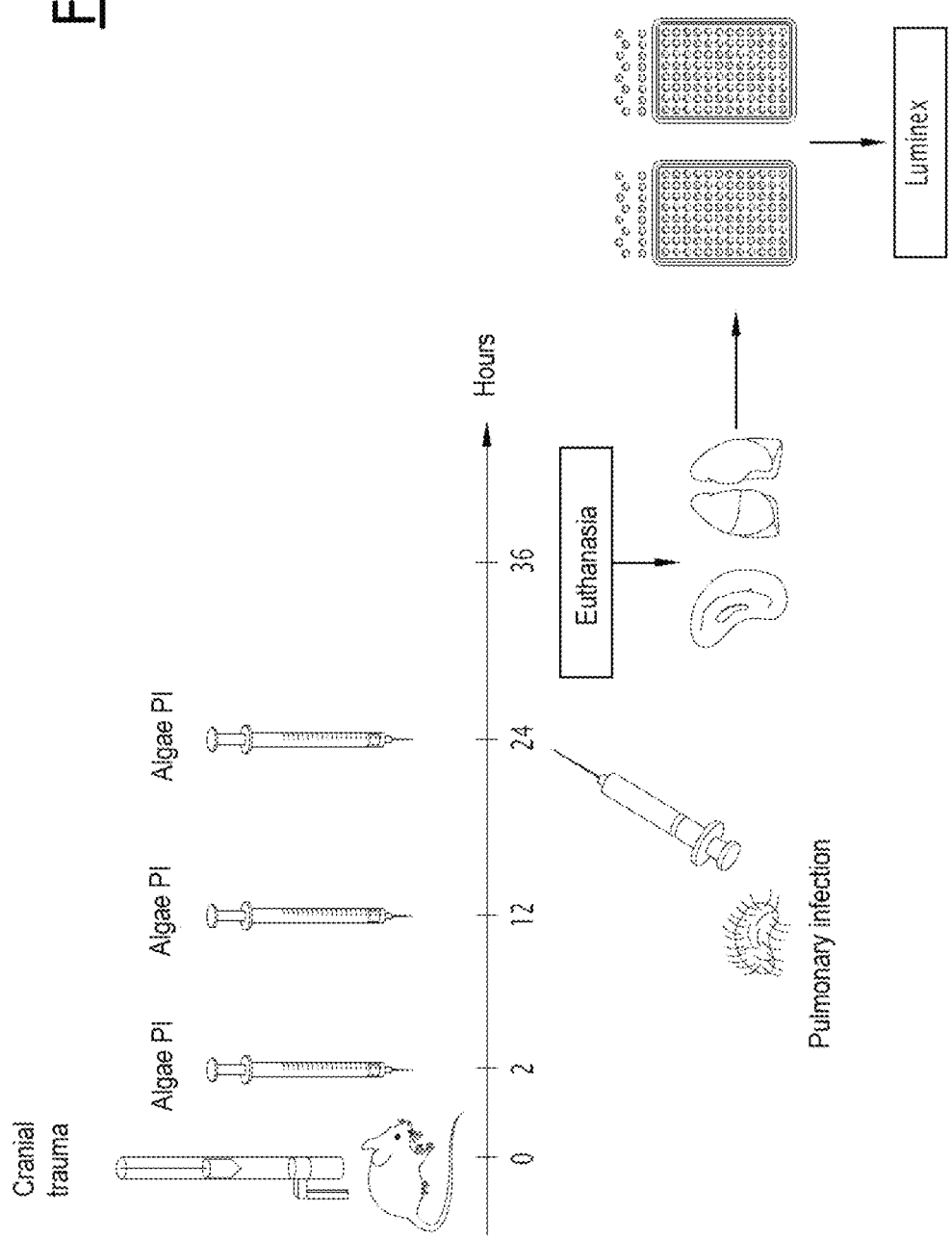

FIG. 13: Diagram schematically representing the experimental protocol for analysis of chemokines in the spleen and lungs using Luminex technique.

Figure 14:
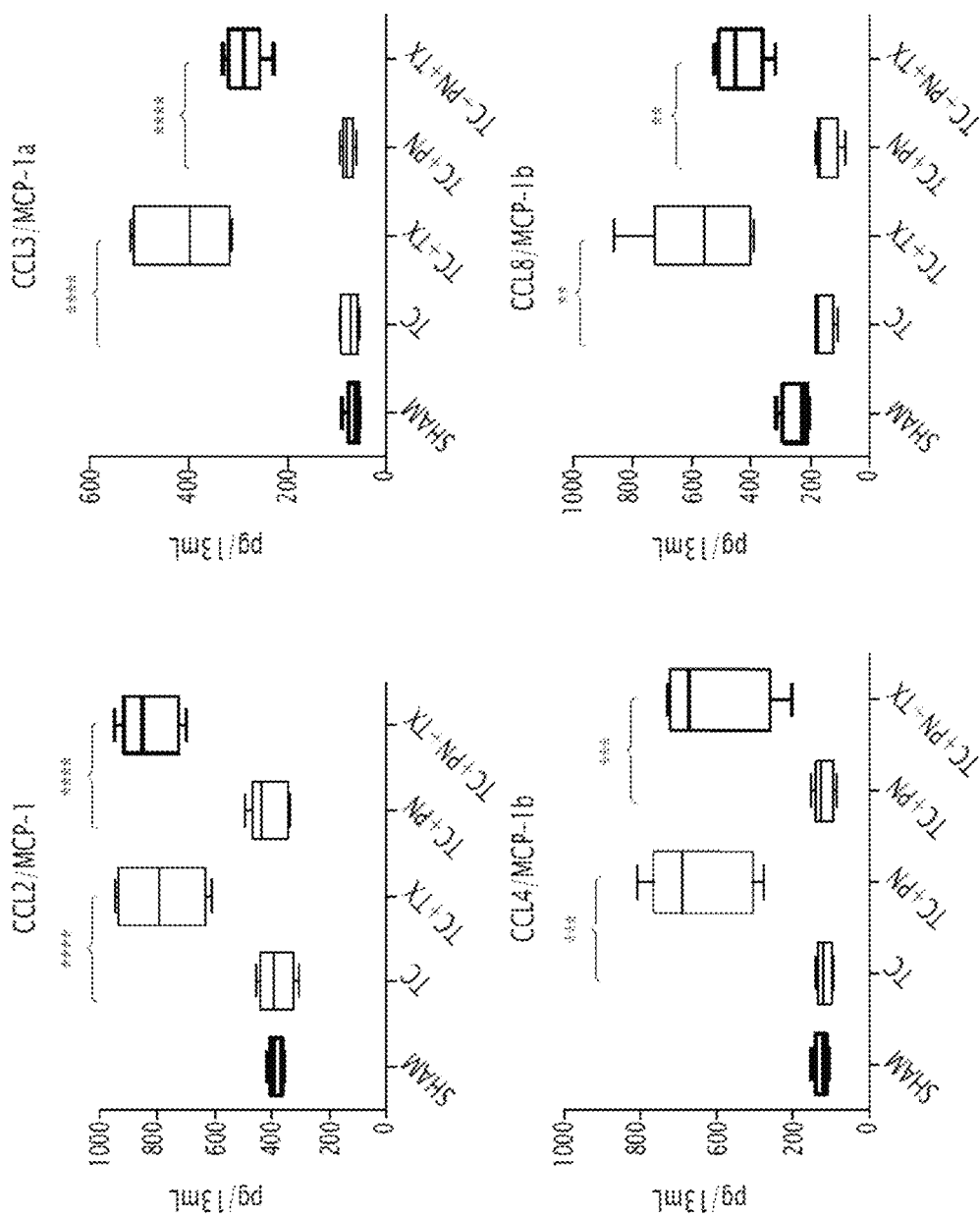

FIG. 14: Administration of polysaccharide in mice with trauma alone, and trauma subjected/infected mice induces an increase in the splenic concentration of the chemokines CCL2, CCL3, CCL4 and CCL8. The mice were divided into 5 groups: Naives (SHAM); trauma alone (TC); TC+treatment with the compound (TC+TX); trauma+pneumonia (TC+PN); and trauma+pneumonia+treatment with the compound (TC+PN+TX). The pneumonia was induced 24 hours after subjecting to TC with the mice being euthanised 12 hrs after the pneumonia onset. The mice in the treated groups received 3 intraperitoneal injections of 200 µg of the marine compound (every 12 hours, starting from TC until euthanasia). The spleens were removed 12 hours after the induction of pneumonia, then ground, and subsequently the level of chemokines CCL2 (A) and CCL3 (B) CCL4 (C) and CCL8 (D) were measured using the Luminex technique. The results are from one experiment (n=5 mice per group). The results are provided as median+/−interquartile ranges *$p<0.001$, **$p<0.0001$.

EXAMPLES

Example 1: Preparation of an Algal Extract for Use According to the Invention

The algal extract is prepared as described in Example 1 of the international patent application WO2015071497.

One tonne of fresh, raw, green algae of type *Ulva*, is washed with fresh water and desanded using an algae washing machine.

Unless otherwise indicated, the steps of the method are carried out at ambient temperature.

The algae (1 tonne of dewatered algae with 8% dry matter) are then ground into fine particles by means of an industrial refiner (brand/model: Inotec "I 175CD-75D"). The term "fine particles" is understood to refer to particles with a size ranging from 50 to 1000 nm, with two populations, the first including particle sizes of between 50 and 200 nm, the second including particle sizes of between 600 and 1000 nm.

The ground material is then pressed using an industrial belt press of the brand/model Flottweg "B FRU 800 HK" at a throughput rate of approximately 1 tonne/hour. This step enables the separation of the solid phase (marc) from the liquid phase (juice). The juice yield obtained is 75%.

The 750 kg of raw juice obtained are then clarified using a disk stack centrifuge of the brand/model Flottweg "AC 2000". This thus produces 710 kg of clear juice with 3.10% dry mass (95 to 98% mass yield) and a cream (2 to 5% mass).

Thereafter, the clear juice is ultra filtered through a 15 KDa ceramic membrane (Tami Industries). Thus a permeate and a retentate are subsequently obtained. The permeate is stored until 640 kg of filtration juice (91% volume yield) with 2.2% dry matter is obtained.

The filtration juice (permeate) is then dried by lyophilisation following concentration by evaporation.

The concentration process is carried out using a single-effect evaporator (EVA 1000, Pignat) with the following parameters: forced recirculation, feeding flow rate 10 L/h, steam pressure of 1 bar, vacuum pressure of 0.3 bar, and evaporation temperature 90° C. A first concentration is carried out with an evaporated water flow rate of 8 L/h and the Brix value rises from 5.5 (equal to a dry matter concentration of 4.5%) to 14.7. This solution is then concentrated a second time with an evaporated water flow rate of 5-6 L/h and the Brix value rises to 34. The dry matter concentration of the solution is determined at 38.4%.

The lyophilisation is then carried out using an apparatus from Bioblock Scientific (model: CHRIST—Alpha 1-4 LSC) at a freezing temperature of −80° C. which is also the minimum temperature during this step.

The powder obtained is then ground with a planetary mill, brand Philips MiniMill. The product was introduced into grinding bowls (10 g of product in each grinding bowl with 4 zirconia balls). The assembly was operated to rotate for 15 minutes at the speed 10. This thus yielded 14 kg of algal extract powder.

Example 2: Study of the Effect of Algal Extract in a Mouse Model of Cranial Trauma (Head Trauma)—Materials and Methods Animal Welfare: All the experiments were carried out in accordance with the principles of laboratory animal welfare. All the experiments have been approved by the Pays de la Loire ethics committee and by the MESR (Ministère de l'Enseignement supérieur, de la Recherche et de l'Innovation/French Ministry of Higher Education, Research and Innovation) (no 2016121915529061). The mice (Swiss males aged 5 weeks, strain RjOrl: SWISS and C57BL/6 males aged 6 weeks, strain C57BL/6JRj weighing 24 to 28 g) were obtained from the Janvier laboratory (Laval). The mice were maintained in a 12-hour day/night cycle with free access to water and food at the animal facility of the Institut de Recherche en Santé 2 (IRS 2) [Institute for Health Research] in Nantes, France.

Algal Extract Comprising Sulfated and Non-Sulfated Polysaccharides: It was extracted and purified from the alga *Ulva armoricana* collected on the beach at Plestin les Grèves (Brittany, France), according to the protocol described in the Example 1. The absence of contamination of the various fractions with LPS was assessed using a commercially available technique (E-toxate Kit, Sigma). No LPS in the final extract was detected by means of this assay. The samples used were in the form of an aqueous solution at a concentration of 1% of sulfated and non-sulfated polysaccharides (concentration by weight of the dry matter relative to the final volume of the solution).

Cranial Trauma Model: The cranial trauma was brought about using the "weight drop device" technique (Flierl et al., 2009, Nat. Protoc.; 4 (9): 1328-37). A subcutaneous injection of 0.1 mg/kg of buprenorphine was administered thirty minutes before the procedure and thereafter the mice were anesthetised by continuous inhalation of isoflurane (flow rate of fresh gas 0.8 L/min, fraction inhaled 3.5%). A 1 cm incision at the top of the skull served to effectively locate the coronal and sagittal sutures and to optimise the procedure. The trauma was then delivered by the dropping of a standardised weight measuring 2.5 cm in height, thereafter the incision was stitched closed with 4.0 sutures. There should be no breach of the skull. The ad integrum recovery was monitored immediately and then every 12 hours, and mice were given subcutaneous buprenorphine analgesia if necessary. In the event of pathological awakening, the mice were euthanised. The endpoints were evaluated according to Table I below:

TABLE I

End Points. The mice were euthanised for a score greater than or equal to 6.

|  | 0 point | 1 point | 2 points | 3 points |
|---|---|---|---|---|
| Weight loss | <5% | 5-12% | 13-20% | >20% |
| Physical appearance (spiky hairs and hunched back) | Normal | Slightly impaired | Moderately impaired | Highly impaired |
| Behaviour (isolation) | Normal | Slightly altered | Moderately altered | Highly altered (permanent isolation from the rest of the group) |

Bacterial Inoculum: The MSSA strain ATCC 29213 (hemolysin positive, Panton Valentine negative leucocidin) was used for all the experiments. The strain was incubated in heart-brain broth for 18 hrs at 37° C., and thereafter was washed 2 times (1000 g for 10 min at 20° C.), and finally was diluted in sterile PBS. Thereafter, the inoculum was calibrated by nephelometry in order to obtain 7 McFarland then finally concentrated 5 times in order to achieve a concentration between 1 and $3\times10^9$ CFU/mL.

Pneumonia Model: A subcutaneous injection of 0.1 mg/kg of buprenorphine was administered thirty minutes before the procedure and thereafter the mice were anesthetised by continuous inhalation of isoflurane (flow rate of fresh gas 0.8 L/min, fraction inhaled 3.5%). The pneumonia was then induced by the intratracheal insertion of a 24-gauge gavage cannula and then by the injection of 75 µL of inoculum. The mice were divided into 4 groups: non-trauma subjected, uninfected, Sham mice (S); non-trauma subjected, infected mice (PN); trauma subjected and infected mice not treated (PN+TC); and trauma subjected and infected mice treated with 200 µg marine compound, administered intraperitoneally every 12 hours (PN+TC+TX).

Administration of the Algal Extract: The algal extract was administered intraperitoneally or intratracheally, in doses of 50 µg, 200 µg and 500 µg in a total volume of 200 µL (supplemented with PBS).

Investigation of a Dose-Effect of the Extract: The algal extract was administered intraperitoneally 2 hours and 12 hours before euthanasia at doses of 50, 200 and 500 µL in a total volume of 200 µL of PBS. In order to stimulate the cells of the pulmonary mucosal immune system in situ, the algal extract was also administered intratracheally, at a dose of 50 µg in 75 µL according to the same procedure as for bacterial inoculation during pneumonia induction. The spleens and lungs were then removed and thereafter the cell populations were analysed by flow cytometry after intra-cellular staining of the pro-inflammatory cytokines (IL-12, TNFα, INF γ).

FACS Analysis of Cell Populations: The pulmonary and spleen cell suspensions were obtained by manual mechanical grinding and then digestion with collagenase for 30 minutes (spleens) or 45 minutes (lungs), and subsequently passed through a screen (pores of 70 µm). After treatment with a red blood cell lysis solution, the cell suspensions obtained were incubated for 30 minutes at 4° C., with the antibodies coupled to the specific fluorochromes.

For DCs: CD24-BV711 (M1/69, BD Horizon), CD11c-PeCy7 (NK18, Biolegend), MHC II-BV421(M5/114.15.2, Biolegend); For macrophages: F4/80-Alexa647(BM8, Biolegend), CD11b-BV605 (M1/70, BD Horizon), CD11c-PeCy7(NK18, Biolegend). For NK cells and T lymphocytes: NK1.1-BV421(PK136, BD Horizon), CD3-PE (145-2C11, eBioscience) and KLRG 1-APC (2F1, eBioscience). The cells were analysed on the BD LSR II® device, and thereafter all of the data were then interpreted using the Flowjo Software® (TreeStar Inc, Ashland, OR).

Staining of Intracellular Cytokines: The mice were euthanised 12 hours after the tracheal instillation of MSSA producing pneumonia. For the intracellular staining of cytokines in DCs, macrophages and lymphocytes, the cells were incubated for 5 hours in a medium comprising Roswell Park Memorial Institute medium (RPMI) and Golgi Plug (BD Bioscience) in order to block exocytosis, washed twice and then labelled according to the membrane markers (see above). The fixation and permeabilisation were carried out according to the manufacturer's recommendations (BD Cytofix/Cytoperm kit, BD Bioscience). The cells were incubated overnight at 4° C. in PermWash with the antibodies anti ID 2-PE (C15.6, BD Pharmingen), INF γ-Alexa488 (XMG1.2, eBioscience) and TNFα-PE (MP6-XT22, BD Pharmingen); then the cells were washed twice and analysed by flow cytometry.

Evaluation of Bacterial Growth and Spread: The lungs and spleens were weighed and then mechanically ground under sterile conditions. The organ homogenates were subjected to several dilutions (from $10^{-2}$ to $10^{-6}$ depending on the conditions) and were incubated at 37° ° C. on a specific medium (Chapman) in order to avoid the growth of other bacteria. After a 24 hour period of incubation, the colonies were counted and the results were expressed in $\log_{10}$ CFU per gram of organ.

The Bactericidal Kinetics: the bactericidal kinetics in a liquid medium was performed using an inoculum of MSSA ATCC 29213 to 0.5 McFarland standard (nephelometric data) diluted 5 times in a Mueller Hinton broth (starting inoculum=$6\times10^6$ CFU/mL). The control was compared with several ranges of concentrations of the marine sulfated compound (50 µg/mL, 200 µg/mL, 500 µg/mL). 50 µL were then plated at H0, H3, H6 and H24 on TS agar and then incubated at 37° C. for 24 hrs. The colonies were counted and the results expressed in $\log_{10}$ CFU/ml.

Determination of the Level of Expression of Pulmonary and Spleen Chemokines by the Luminex Method. After removing samples of the lungs and spleens, the latter were mechanically homogenised at 4° C. in the presence of lysis buffer (1×PBS, pH 7.4/0.1% triton X-100) containing 1 mM of protease inhibitor cocktail (Sigma, Isle D'Abeau Chesnes, France). The homogenates were then centrifuged at 12,000 g for 20 minutes at 4° C., thereafter the supernatant was removed and then stored at −80° C. until the analysis. The concentrations of the different chemokines were produced by using the CIMNA platform (Centre d'Immunomonitorage Nantes Atlantique/Nantes Atlantique Immunomonitoring Centre) using the Luminex® method after specific labelling of the different chemokines: CCL19/MIP-3 beta (BR19), CCL2/MCP-1/JE (BR18), CCL20/MIP-3 alpha (BR48), CCL21/6Ckine (BR72), CCL3/MIP-1 alpha (BR46), CCL4/MIP-1 beta (BR51), CCL8/MCP-2 (BR38), CXCL1/KC (BR13), CXCL10/IP-10 (BR37), CXCL2/MIP-2 (BR20).

Magnetic Sorting of NK Cells: The pulmonary cell suspensions were obtained according to the protocol used for the FACS analysis. The cells were counted (approximately $2 \cdot 10^7$ per lung) and then centrifuged at 300 g for 10 minutes. The cells were suspended in 40 μL of FACS Buffer for $10^7$ cells and then labelled with 10 μL of NK Cell Biotin—Antibody Cocktail (Miltenyi Biotec®, Germany) and incubated for 5 minutes at 4° C. After a further centrifugation at 300 g for 10 minutes, the cells were incubated for 10 minutes at 4° C. with 20 μL of Anti-Biotin MicroBeads (Miltenyi Biotec®, Germany) for $10^7$ cells. Finally, the magnetic separation was carried out according to the recommendations of the manufacturer (Miltenyi Biotec, Germany). Each group (naive and TC) was comprised of 6 mice, then the lungs were ground two at time in order to achieve at a minimum 10,000 NK cells per well (for a total of approximately 20 million cells per mouse lung) The purity of NK cells was greater than 90%.

In Vitro Stimulation of NK Cells: The NK cells isolated after magnetic sorting were stimulated in vitro for 5 hours in the $CO_2$ oven at 37° C. and under 3 different conditions: Control (RPMI+FBS [foetal bovine serum]+IL-2 at a concentration of 3000 IU/mL), Algae (control+Algae at 500 μg/mL) and PMA-Ionomycin (control+PMA at 50 ng/mL and Ionomycin (1 μg/mL). The cells were also stimulated 4 hours out of 5 with Golgi Plug (BD Bioscience) according to the manufacturer's recommendations. The secretion of IFN-g, the membrane expression of KLRG 1, and the number of NK cells were then analysed by FACS.

In Vivo Depletion of NK Cells: The NK cells were depleted in vivo by IV (retro-orbital) injections of 10 μL of LEAF purified anti mouse NK1.1 (clone PK136/cat #108712—1 mg/mL) (Biolegend) in 190 μL of PBS. The injections were administered 2 h and 48 h after the cranial trauma. The efficacy of NK cell depletion was evaluated using FACS by counting the number of pulmonary NK cells: NK1.1-BV421(PK136, BD Horizon), CD3-PE (145-2C11, eBioscience).

Statistics: The statistical analyses were performed with the software application GraphPadPrism 6.0® (San Diego, CA, United States). The nonparametric continuous variables were expressed in medians+/−interquartile ranges and analysed by a Kruskall-Wallis test with post-hoc use of the Dunn test. The analyses of the populations in percentage terms were performed by a bilateral Fisher test.

Example 3: Clinical and Bacteriological Effects

The mice were divided into 4 groups: Sham (S); Pneumonia only (PN); Cranial Trauma+Pneumonia (TC+PN); and trauma subjected and infected mice, treated every 12 hrs by intraperitoneal injection (IP) of 200 μg of the compound (TC+PN+TX), starting 2 hours after trauma and until euthanasia. The mice of groups S and PN received an incision of 1 cm from the top of the skull without trauma. The pneumonia was induced 24 hours after the cranial trauma. Euthanasia occurred 24 to 48 hours after the induction of pneumonia according to the criteria studied (FIG. 1).

The Algal Extract has No Effect on Weight Loss in Trauma Subjected and Secondarily Infected Mice The MSSA pneumonia induces a transient weight loss of around 12% of body weight after 24 hours. The cranial trauma increases the weight loss in the initial stage of infection but does not affect recovery from D+3 as compared to non-trauma subjected mice. The treatment had no effect on weight loss in the trauma subjected and secondarily infected mice (FIG. 2).

The Algal Extract Limits Bacterial Spread in Trauma Subjected Mice 48 Hours after the Induction of MSSA Pneumonia The pulmonary bacterial loads are similar in all the groups infected at 24 hrs (PN, TC+PN, TC+PN+TX) (FIG. 3A) as well as at 48 hrs (FIG. 3B) following the induction of pneumonia.

From the 24th hour following lung infection, all mice with pneumonia were MSSA bacteremic (splenic bacterial load>2 log).

The trauma subjected mice do not show higher bacterial spread after pneumonia compared to non-trauma subjected mice (PN vs TC+PN) (FIGS. 3C and 3D).

The treatment had no effect on bacteremia at 24 hrs following the infection (FIG. 3C) but at the 48th hour of the infection, *Staphylococcus aureus* was detected in 22% of the mice in the treated group (TC+PN+TX) versus 100% in the group subjected to post-traumatic pneumonia not treated (TC+PN). The mice in the group treated with the algal extract thus present low spleen bacterial loads at 48 hours from the induction of pneumonia (FIG. 3D). This effect seems to be related to the frequency of administration because the single injection of the algal extract induces a reduction in the bacteremia which is less than that observed in the case of multiple injections (results not shown).

Although there is no difference in bacterial load between the pneumonia alone group (PN) and the infected trauma subjected group (CT+PN) (FIGS. 3C and 3D), the adjuvant treatment (injected before infection) decreases the bacterial spread during post-traumatic infections (FIG. 3D), but not in the absence of trauma (FIG. 3E). This result suggests that the algal extract improves the pulmonary response to a bacterial infection in the event of post-traumatic immunosuppression, but has little or no effect on healthy animals during pneumonia.

The Algal Extract has No Specific Anti-MSSA Activity In Vitro

During post-traumatic pneumonia, the treatment reduces the duration of systemic spread of the bacterial infection (FIG. 3). This therapeutic effect could be linked either to a direct antibacterial effect of the algal extract, or to an effect on the immunity of the host. In order to study the potential direct antibacterial properties, we evaluated the effect of the algal extract on the MSSA ATCC 29213 strain. In order to do this in vitro evaluation of the effects of the algal extract on the growth of MSSA was performed by applying the method of bactericidal kinetics in liquid medium. The results show that the algal extract has no direct anti-MSSA effect regardless of the concentration tested, including at supra-therapeutic doses (50, 200 and 500 µg/mL) (FIG. 4).

Example 4: Investigation of an Immunostimulatory Effect of the Algal Extract in Naive Mice The clinical effects of the algal extract on bacterial spread (FIG. 3D), its lack of anti-MSSA effect in vitro (FIG. 4) as well as its lack of clinical action in the absence of trauma (FIGS. 3E and F) have led to the investigation of an immunostimulatory effect of the polysaccharide. A dose-effect relationship of the extract on the secretion of pro-inflammatory cytokines (IL-12 by DCs, TNFα by macrophages, and INF γ by NKs and TLs) in the lungs and spleen was first investigated in naive mice. The evaluation of cytokine production was performed by flow cytometry after intracellular staining. For this purpose, the extract was injected multiple times (2 hours and 12 hours before euthanasia) intraperitoneally. The extract was also administered intra-tracheally in an attempt to induce direct stimulation of cells of the pulmonary mucosal immune system.

Intra-Peritoneal Administration of the Algal Extract 2 Hours and 12 Hours Before Euthanasia does not Induce an Increase in the Production of Pro-Inflammatory Cytokines (IL-12, TNFα, INF γ) in Naive Mice The algal extract does not induce an increase in the percentage of IL-12 producing pulmonary DCs (FIG. 5A), regardless of the dose used. It does not increase the proportion of TNFα-producing macrophages (FIG. 5B) or increase the number of NK cells (FIG. 5C) or INFγ$^+$ TLs in lung tissue. The total numbers of pulmonary CDs, NKs and TLs were not altered by the injection of the algal extract in the naive mice.

The effects of administration of the algal extract were also evaluated 12 hours after the intraperitoneal injection of the compound. The same dosages have been studied. At 12 hrs, there was no difference noted for the production of pro-inflammatory pulmonary cytokines as well as for the number of cells (data not shown).

Intra-Tracheal Administration of the Algal Extract 2 Hours and 12 Hours Before Euthanasia does not Induce an Increase in the Production of Pro-Inflammatory Cytokines (IL-12, TNFα, INF γ) in Naive Mice Since the intraperitoneal route had little effect in naive mice on the immune cells studied, the effect of a treatment administered directly by the intra-tracheal route was tested. The production of cytokines was assessed 2 hrs (T (H-2)) and 12 hrs (T (overnight)) after the intratracheal instillation of the algal extract. No evident difference in secretion was demonstrated as compared to the control mice (Naives) and to the administration of LPS, at a dose of 50 µg, 2 hours before euthanasia (LPS (H-2)) (FIG. 6).

Example 5: Investigation of the Immunostimulatory Effect of the Algal Extract in a Post-Traumatic Immunosuppression Model The lack of immunostimulatory effect of the algal extract in naive mice has led to continuing investigation in a model of trauma subjected and secondarily infected mice, reproducing the scenario observed in a clinical setting. The immunostimulatory effect of the algal extract was thus evaluated in a post-traumatic immunosuppression model. The cranial trauma was brought about in C57/Bl6 male mice, then the algal extract was administered intraperitoneally at a dose of 200 µg, starting from two hours after the trauma and then every 12 hours until euthanasia (3 injections in total). The pneumonia was induced 24 hours after the cranial trauma and subsequently the mice were euthanised 12 hours after the pneumonia. The mice were divided into 4 groups: Sham (S); pneumonia only (PN); cranial trauma+pneumonia not treated (TC+PN); and cranial trauma+pneumonia treated with algal extract (TC+PN+TX) (FIG. 7).

Administration of the Algal Extract does not Increase the Percentage of Pulmonary Innate Immune Cells Producing Pro-Inflammatory Cytokines In a post-traumatic pneumonia model, intraperitoneal administration of the algal extract does not increase the proportion of: IL-12 producing DCs (FIG. 8A), TNFα-producing macrophages (FIG. 8B), or INFγ producing NKs or TLs (FIG. 8C).

Administration of the Algal Extract Increases the Number of Interferon γ-Producing NK Cells Cranial trauma induces a decrease, in the lungs, in the total number of NK cells (FIG. 9A), as well as a decrease in interferon γ producing NK cells ($p<0.01$) (FIG. 9B). Administration of the algal extract induces an increase in the number of total NK cells and interferon γ producing NK cells in the lung (FIGS. 9A and 9B) ($p<0.05$) without increasing the percentage of INFY+cells (FIG. 8C). This effect is not found as clearly for T lymphocytes even if there is an emerging trend ($p=0.17$) (FIG. 9C).

Example 6: In Vitro Investigation of a Direct Effect of the Algal Extract on the NK Cells of Naive and Trauma Subjected Mice The algal extract has no effect in vitro on secretion of interferon γ or expression of the activation factor KLRG1 by the pulmonary NK cells.

Given the increase in the number of interferon γ producing NK cells in the mice treated with the extract, and the absence of an increase in the level of the chemokines CXCL-1 and CXCL-2, it was investigated as to whether the effect found in vivo was due to a direct action of the treatment on NK cells. For this, the pulmonary NK cells of naive and trauma subjected mice were magnetically sorted and then stimulated in vitro for 5 hours under 3 conditions: Control (Ctrl), algal extract, and PMA+Ionomycin (PMA+Iono). Unlike stimulation with PMA-Iono, the stimulation in vitro with the algal extract does not induce an increase in the production of interferon γ (FIG. 10B) or of the activation marker KLRG 1 by the NK cells (FIG. 10C). The number of NK cells was not different in the different groups after 5 hours of stimulation. (FIG. 10D).

Example 7: Investigation of the Bacteriological Effect in the Case of Depletion of NK Cells in Vivo The mice were divided into 3 groups: Trauma subjected and infected mice (TC+PN); trauma subjected mice, infected and NK cell depleted (TC+PN+del); and trauma subjected, infected mice, NK cell depleted and treated with algal extract (TC+PN+del+TX). The pneumonia was induced 24 hours after the cranial trauma. Euthanasia occurred 48 hours after the induction of pneumonia. The depletion of NK cells was brought about 2 hrs and 48 hrs after the cranial trauma. The spleen bacterial loads as well as the efficacy of pulmonary NK cell depletion (FACS) were analysed at 48 hrs following the induction of pneumonia (FIG. 11).

The Algal Extract does not Limit the Splenic Bacterial Spread in Trauma Subjected, NK Cell Depleted Mice In order to assess whether the effects of the algal extract on the splenic bacterial spread were due to the increase in the number of pulmonary NK cells, it was evaluated as to whether this effect on bacteremia was found in the event of NK cell depletion in vivo.

In the absence of pulmonary NK cells (depletion greater than 95%), there are no noted effects of the algal extract on the splenic bacterial spread at 48 hours from the infection (TBI+PN+del vs TBI+PN+del+TX) (FIG. 12).

Example 8: Study of the Effect of the Algal Extract on the Secretion of Splenic and Pulmonary Chemokines The administration of the sulfated polysaccharide induces an increase in the number of pulmonary NK cells in trauma subjected and infected mice. In order to determine whether this increase in number was due to a recruitment of NK cells to the lung by the inducing of a secretion of chemokines, the splenic and pulmonary secretions of the chemokines CXCL1 (KC), CCL2(MCP-1), CCL19(MIP-3b), CXCL2(MIP-2), CXCL10(IP-10), CCL8(MCP-2), CCL3(MIP-1a), CCL20 (MIP-3a), CCL4(MIP-1b), and CCL21(6Ckine) were evaluated in Luminex. These chemokines are involved in the chemoattraction of NK cells after acute inflammation.

The mice were divided into 7 groups: Naive mice (SHAM); mice trauma subjected only (TC); mice trauma subjected and treated with the compound (TC+TX); mice infected only (PN) (only for studies of pulmonary chemokines); mice infected and treated with algal extract (PN+TX) (only for the study of pulmonary chemokines); mice trauma subjected and infected (TC+PN); and mice trauma subjected, infected and treated with algal extract (TC+PN+TX). The pneumonia was induced 24 hours after the cranial trauma. Euthanasia occurred 12 hours after the induction of pneumonia. The splenic and pulmonary levels of the above-mentioned chemokines were analysed by the Luminex technique (FIG. 13).

The algal extract results in an increase in the spleen levels of the chemokines CCL2, CCL3, CCL4 and CCL8 (FIG. 14). The algal extract has no effect on the splenic secretion of the chemokines CXCL1, CCL19, CXCL2, CXCL10, CCL20, CCL4, CCL21 (data not shown). The intraperitoneal injection of the algal extract also does not result in an increase in the levels of chemokines analysed in the lungs (data not shown).

CONCLUSIONS

A clinical effect of algal extract was initially investigated in a model of post-traumatic bacterial pulmonary infection. No evident effect was demonstrated on the pulmonary bacterial load but this treatment limited the systemic bacterial spread at 48 hours following the infection (splenic bacterial load) in trauma subjected mice. This effect is due to a restoration of the immune functions paralysed by the trauma and not due to a direct antibacterial activity, given that the algal extract has no anti-MSSA activity in vitro and no effect on the bacterial spread in the infected, non-trauma subjected mouse.

The reduction in bacterial spread observed in the murine model of post-traumatic pneumonia after treatment with algal extract as well as the preliminary data established in vitro led to the in vivo investigation in naive mice of a dose-effect relationship of the extract on innate immune system cells (DCs, macrophages, and lymphoid cells NKs and TLs). The doses of 50, 200 and 500 µg/mouse were selected in connection with preliminary toxicity data established in vivo (tests carried out by the Laboratoire Effimune, Nantes, France). The injection times (2 hours and 12 hours before the sacrifice) were selected in order to effectively demonstrate an increase in the secretion of IL-12, TNF a, and INFγ, however no effect was found either in the lung or the spleen. The algal extract also did not induce an increase in membrane expression of MHC II by dendritic cells (data not shown). In the absence of immunosuppression, administration of the algal extract does not induce stimulation of the innate immune cells. This corroborates the bacteriological results in which the administration of the extract of algae, in the absence of trauma (and therefore immunosuppression), does not limit the bacterial spread, contrary to what is observed in the trauma subjected and infected mice.

A stimulation of the secretion of pro-inflammatory cytokines was therefore investigated in a model of trauma subjected mice in which MSSA pneumonia was induced at 24 hours following the trauma. The intraperitoneal injection of algal extract every 12 hrs (starting from TC until euthanasia, that is 3 in total) did not increase the proportion of innate immune cells producing pro-inflammatory cytokines. However, the number of total pulmonary NK cells and the INFγ producing subgroup (cells of interest in the context of an acute pulmonary infection) were increased in the group of mice treated with the marine extract. This increase was found only at the site of infection (no difference found in the spleen). The cranial trauma therefore induces a significant reduction in the number of INFγ producing NK cells, a reduction partially offset by the administration of the algal extract. This effect was not significant for T lymphocytes.

The question therefore arose as to whether an increase in the number of pulmonary NK cells alone is sufficient to explain the limitation of bacterial spread at 48 hours following infection in the treated mice. The NK cells are essential to the antibacterial response, especially in acute pulmonary infection. In addition, in this clinical situation, the action of NK cells is not limited to the secretion of pro-inflammatory substances but leads to a co-stimulation of the other innate immune system cells, in particular by reducing the apoptosis of polynuclear neutrophils and preserving their functional capacities. NK cells also play an immunomodulating role by destroying unactivated DCs and overactivated macrophages that can cause tissue damage. In this context, the effect of the extract was evaluated on the splenic bacterial spread in a post traumatic immunosuppression model in NK cell depleted mice. The effects of the extract on the spleen bacterial load were not noted in the case of NK cell depletion (more than 95% depletion of pulmonary NK cells), confirming the role of these cells in the action of the marine extract in vivo.

The secretion of chemokines in response to the injection of the algal extract, in particular by the epithelial cells via the TLR4/NF-κB pathway, is one of the hypotheses which may explain the increase in the number of NK cells at the infection sites. Thus, the pulmonary and spleen levels of the main chemokines involved in the chemotaxis of NK cells in case of acute inflammation were measured: CXCL1(KC), CCL2(MCP-1), CCL19(MIP-3b), CXCL2(MIP-2), CXCL10(IP-10), CCL8(MCP-2), CCL3(MIP-1a), CCL20 (MIP-3a), CCL4(MIP-1b), CCL21(6Ckine) before and after injection of the algal extract. The study of these chemokines by the Luminex technique made it possible to empirically demonstrate an increase in secretion of the chemokines CCL2, CCL3, CCL4 and CCL8 in the spleen. The injection of the algal extract was found to have no effect either on the secretion of pulmonary chemokines at the time of study, or for the other chemokines in the spleen.

Multiple hypotheses are thus possible: 1) the peak of secretions of pulmonary chemokines would effectively not have been demonstrated possibly due to its occurrence earlier 2) other intermediate signalling pathways are involved in the increase in the number of NK cells in the lungs. The chemokines CCL2, CCL3, CCL4 and CCL8 are mainly secreted by epithelial and endothelial cells and enable the recruitment of immune cells (neutrophils, NK cells, Lymphocytes) in particular after an acute lung injury.

Finally, it was investigated as to whether the algal extract had a direct effect on NK cells whereof the membrane or intracellular expression of TLR 4 receptor is debated in the literature. For this purpose, the pulmonary NK cells from naive and trauma subjected mice were isolated by magnetic sorting and stimulated in vitro by the algal extract in the presence of IL-2. No effect was detected on INFγ secretion, membrane expression of KLRG1, as well as on the number of NK cells per well. The mechanisms of action of the algal extract therefore remain to be elucidated.

The invention claimed is:

1. A method for the prevention and/or treatment of a complication induced by post-traumatic immunosuppression in a subject in need thereof, said method comprising the administration to said subject of an effective amount of an algal extract of the order Ulvales comprising sulfated and non-sulfated polyanionic polysaccharides the molecular weight of which is less than or equal to 50 kDa, wherein the algal extract has no direct antibacterial effect and no direct effect on *Staphylococcus aureus*.

2. The method according to claim 1, for treatment of a septic complication associated with post-traumatic immunosuppression.

3. The method according to claim 2, wherein the said septic complication is a nosocomial infection.

4. The method according to claim 1, wherein the said post-traumatic immunosuppression occurs as a consequence of one or more severe traumas.

5. The method according to claim 1, wherein the said algal extract is an extract of green algae of the type *Ulva*.

6. The method according to claim 1, wherein the said sulfated and non-sulfated polyanionic polysaccharides the molecular weight of which is less than or equal to 50 kDa, have a molecular weight that is less than 15 kDa.

7. The method according to claim 6, wherein the algal extract does not comprise sulfated or non-sulfated polyanionic polysaccharides having a molecular weight that is greater than 15 kDa.

8. The method according to claim 1, wherein the algal extract comprises:
   mannose; and/or
   arabinose; and/or
   galactose; and/or
   glucose; and/or
   rhamnose; and/or
   xylose; and/or
   glucuronic acid.

9. The method according to claim 1, wherein the algal extract comprises:
   from 10 to 50% carbon;
   from 1 to 10% hydrogen;
   from 1 to 5% nitrogen;
   from 20 to 50% oxygen; and
   from 1 to 15% sulfur;
   as a percentage by mass of the total dry matter (dry weight) of the algal extract.

10. The method according to claim 1, wherein the algal extract is obtained by a method of preparation in which:
    a) the algae are washed and desanded;
    b) the said algae are ground;
    c) the solid phase of the ground material is separated from its liquid phase;
    d) the said liquid phase is clarified;
    e) the juice obtained in step d) is ultra filtered through a membrane having pore size of 50 kDa or less; and
    f) the filtration juice obtained in step e) is concentrated and then dried.

11. The method of claim 3, wherein the nosocomial infection is selected from the group consisting of: pneumopathies, urinary tract infections, infections of central venous catheters, and bacterial cerebromeningeal infections.

12. The method of claim 4, wherein the severe traumas is a severe cranial trauma.

13. The method of claim 1, wherein said sulfated and non-sulfated polyanionic polysaccharides the molecular weight of which is less than or equal to 50 kDa, have a molecular weight that is less than 15 kDa, and greater than 500 Da.

14. The method according to claim 2, wherein the said post-traumatic immunosuppression occurs as a consequence of one or more severe traumas.

15. The method according to claim 3, wherein the said post-traumatic immunosuppression occurs as a consequence of one or more severe traumas.

16. The method according to claim 2, wherein the said algal extract is an extract of green algae of the type *Ulva*.

17. The method according to claim 3, wherein the said algal extract is an extract of green algae of the type *Ulva*.

18. The method according to claim 4, wherein the said algal extract is an extract of green algae of the type *Ulva*.

19. The method according to claim 2, wherein the said sulfated and non-sulfated polyanionic polysaccharides the molecular weight of which is less than or equal to 50 kDa, have a molecular weight that is less than 15 kDa.

20. The method according to claim 3, wherein the said sulfated and non-sulfated polyanionic polysaccharides the molecular weight of which is less than or equal to 50 kDa, have a molecular weight that is less than 15 kDa.

* * * * *